(12) United States Patent
Choi et al.

(10) Patent No.: US 10,238,355 B2
(45) Date of Patent: Mar. 26, 2019

(54) TOMOGRAPHY APPARATUS AND METHOD OF RECONSTRUCTING TOMOGRAPHY IMAGE THEREOF

(71) Applicant: Samsung Electronics Co., Ltd, Gyeonggi-do (KR)

(72) Inventors: Ji-young Choi, Gyeonggi-do (KR); Toshihiro Rifu, Gyeonggi-do (KR); Kyoung-yong Lee, Gyeonggi-do (KR); Duhgoon Lee, Gyeonggi-do (KR)

(73) Assignee: Samsung Electronics Co., Ltd., Suwon-si (KR)

(*) Notice: Subject to any disclaimer, the term of this patent is extended or adjusted under 35 U.S.C. 154(b) by 123 days.

(21) Appl. No.: 15/435,232

(22) Filed: Feb. 16, 2017

(65) Prior Publication Data
US 2017/0258432 A1    Sep. 14, 2017

(30) Foreign Application Priority Data

Mar. 10, 2016  (KR) .......................... 10-2016-0029094

(51) Int. Cl.
*A61B 6/00* (2006.01)
*A61B 6/03* (2006.01)
(Continued)

(52) U.S. Cl.
CPC ............ *A61B 6/5205* (2013.01); *A61B 6/032* (2013.01); *A61B 6/037* (2013.01); *A61B 6/463* (2013.01);
(Continued)

(58) Field of Classification Search
CPC ......... A61B 6/032; A61B 6/037; A61B 6/463; A61B 6/503; A61B 6/5205; A61B 6/5264; A61B 6/563
See application file for complete search history.

(56) References Cited

U.S. PATENT DOCUMENTS 6,466,640 B1   10/2002  Taguchi
6,865,250 B2    3/2005  Londt et al.
(Continued)

FOREIGN PATENT DOCUMENTS

KR   1020150095184    8/2015
KR   1020150099375    8/2015

OTHER PUBLICATIONS

Notification of International Search Report and Written Opinion of the International Searching Authority dated Jan. 10, 2017, 11 pages.
(Continued)

*Primary Examiner* — Dani Fox

(57) ABSTRACT

A tomography apparatus includes a data obtainer and an image processor. The data obtainer performs a tomography scan on a moving object and obtains raw data of the object The image processor reconstructs a first tomography image of the object for a first slice section in a first phase from the raw data and reconstructs a second tomography image in a second phase, which is different from the first phase, for the first slice section of the object by using the raw data. The image processor also generates motion information indicating a three-dimensional (3D) motion of the object. The second phase is a phase beyond a phase range of the raw data.

20 Claims, 27 Drawing Sheets

(51) Int. Cl.
*G06T 11/00* (2006.01)
*A61B 6/02* (2006.01)

(52) U.S. Cl.
CPC ............ *A61B 6/503* (2013.01); *A61B 6/5264* (2013.01); *A61B 6/5288* (2013.01); *A61B 6/563* (2013.01); *G06T 11/006* (2013.01); *A61B 6/027* (2013.01)

(56) References Cited

U.S. PATENT DOCUMENTS

| | | | |
|---|---|---|---|
| 7,684,537 B2* | 3/2010 | Imai | A61B 6/405 |
| | | | 378/16 |
| 8,055,050 B2 | 11/2011 | Roessl et al. | |
| 2002/0025018 A1 | 2/2002 | Takagi et al. | |
| 2004/0120446 A1 | 6/2004 | Londt et al. | |
| 2007/0086563 A1 | 4/2007 | Bruder | |
| 2008/0137936 A1 | 6/2008 | Boese et al. | |
| 2008/0317196 A1 | 12/2008 | Imai et al. | |
| 2010/0208962 A1 | 8/2010 | Roessl et al. | |
| 2014/0301622 A1 | 10/2014 | Forman | |
| 2015/0223771 A1 | 8/2015 | Lee et al. | |
| 2015/0243045 A1 | 8/2015 | Ra et al. | |

OTHER PUBLICATIONS

Seungeon Kim, et al., Cardiac Motion Correction Based on Partial Angle Reconstructed Images in X-Ray CT, Medical Physics, vol. 42, No. 5, May 2015, 13 pages.

Tuncay Hazirolan, et al., "Myocardial Bridging on MDCT", American Roentgen Ray Society, www.ajronline.org, Apr. 2007, 7 pages.

European Patent Office, "Supplementary European Search Report," Application No. EP 16893691.2, Oct. 19, 2018, 10 pages.

J. Van Stevendaal, et al., "A motion-compensated scheme for helical cone-beam reconstruction in cardiac CT angiography," American Association of Physicists in Medicine, Medical Physics, vol. 35, No. 7, Jul. 2008, 13 pages.

* cited by examiner

TOMOGRAPHY APPARATUS AND METHOD OF RECONSTRUCTING TOMOGRAPHY IMAGE THEREOF

CROSS-REFERENCE TO RELATED APPLICATION(S) AND CLAIM OF PRIORITY

The present application is related to and claims the benefit of Korean Patent Application No. 10-2016-0029094, filed on Mar. 10, 2016, in the Korean Intellectual Property Office, the disclosure of which is incorporated herein in its entirety by reference.

TECHNICAL FIELD

The present disclosure relates to tomography apparatuses and methods of reconstructing tomography images thereof.

BACKGROUND

Medical imaging apparatuses are used to obtain images of internal structures of objects. Medical imaging apparatuses that are non-invasive testing apparatuses capture and process images of structural details, internal tissues, and the flow of fluids in human bodies and provide the images to users. The users who are, for example, medical doctors, may diagnose health states and diseases of patients by using medical images output from the medical imaging apparatuses.

Examples of an apparatus for imaging an object by projecting X-rays toward a patient include a computed tomography (CT) apparatus.

A CT apparatus that is a medical imaging apparatus or a tomography apparatus may provide a cross-sectional image of an object and may clearly show internal structures (e.g., organs such as kidney and lung) of the object without overlapping them, unlike a general X-ray apparatus, and thus is widely used to accurately diagnose a disease. A medical image obtained by a tomography apparatus is referred to as a 'tomography image'. An image captured by a CT apparatus may be referred to as a CT image.

However, when a tomography apparatus captures an object that moves, a state of the object changes as time passes, and thus it is difficult to obtain a tomography image at a desired time and in a desired phase. For example, when a tomography scan is performed on the heart, in order to reconstruct a tomography image in a target phase, an electrocardiogram (ECG) of a patient is continuously monitored and imaging is performed at a time corresponding to the target phase. Since complicated processes for monitoring an ECG and setting an accurate imaging time have to be performed, complexity in system control is increased.

SUMMARY

Objectives of embodiments are to obtain tomography images in target phases by imaging moving objects without restrictions of imaging times, and more particularly, to obtain tomography images in predetermined phases irrespective of phases of raw data obtained by performing tomography scans.

Also, objectives of embodiments are to minimize skewness and motion artifacts in tomography images by imaging moving objects at high pitches and reconstructing images in target phases through motion compensation.

Also, objectives of embodiments are to reconstruct images in wide z-axis ranges and various phases even when moving objects are imaged at high pitches.

Additional aspects will be set forth in part in the description which follows and, in part, will be apparent from the description, or may be learned by practice of the presented embodiments.

To address the above-discussed deficiencies, it is a primary object to provide a tomography apparatus which includes: a data obtainer configured to perform a tomography scan on a moving object and obtain raw data of the object; and an image processor configured to reconstruct a first tomography image of the object for a first slice section in a first phase from the raw data and reconstruct a second tomography image in a second phase, which is different from the first phase, for the first slice section of the object by using the raw data and motion information indicating a three-dimensional (3D) motion of the object, wherein the second phase is a phase beyond a phase range of the raw data.

The data obtainer may perform a tomography scan on the object over an angular range including at least one pair of facing angular sections, and the image processor may reconstruct one pair of images corresponding the at least one pair of facing angular sections by using the raw data, and obtains the motion information by using the one pair of images.

The data obtainer may obtain the raw data in a first phase range that is shorter than one cycle of motion of the object, and the image processor may reconstruct a plurality of the second tomography images having different phases from each other in the one cycle of motion of the object from the raw data.

The object may be the heart.

The first phase may be a phase with a lowest motion speed in one cycle of motion of the object.

The motion information of the object may be previously stored.

The tomography apparatus may further include: a display configured to display the first tomography image; and an input device configured to receive a user input that selects a phase, wherein the image processor reconstructs the second tomography image of the object in the second phase, which is different from the first phase, in response to the user input that selects the second phase, wherein the display displays the second tomography image.

The data obtainer may include: a table configured to move the object along a first axis; an X-ray generator configured to rotate around the object at a constant speed on a plane perpendicular to the first axis and irradiate X-rays; and an X-ray detector configured to detect the X-rays, wherein the data obtainer obtains the raw data by detecting the irradiated X-rays in the X-ray detector while the object is moved along the first axis and the X-ray generator rotates around the object.

The tomography apparatus may further include: a display configured to display the first tomography image; and an input device configured to receive a user input that selects at least one of a phase and a position of the object on the first axis, wherein the image processor reconstructs a tomography image in the selected phase from a tomography image in the first phase obtained at the selected position on the first axis, wherein the display displays the second tomography image.

The object may be the heart, wherein the image processor reconstructs a diastolic tomography image corresponding to diastole of the heart as the first tomography image in the first phase, reconstructs a systolic tomography image corresponding to systole of the heart as the second tomography image in the second phase, and determines whether a myocardial bridge occurs by comparing the diastolic tomography image with the systolic tomography image.

According to an aspect of another embodiment, a method of reconstructing a tomography image includes: performing a tomography scan on a moving object and obtaining raw data of the object; reconstructing a first tomography image of the object for a first slice section in a first phase from the raw data; and reconstructing a second tomography image in a second phase, which is different from the first phase, for the first slice section of the object by using the raw data and motion information indicating a three-dimensional (3D) motion of the object, wherein the second phase is a phase beyond a phase range of the raw data.

According to an aspect of another embodiment, a computer-readable recording medium stores a program code for executing the method.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
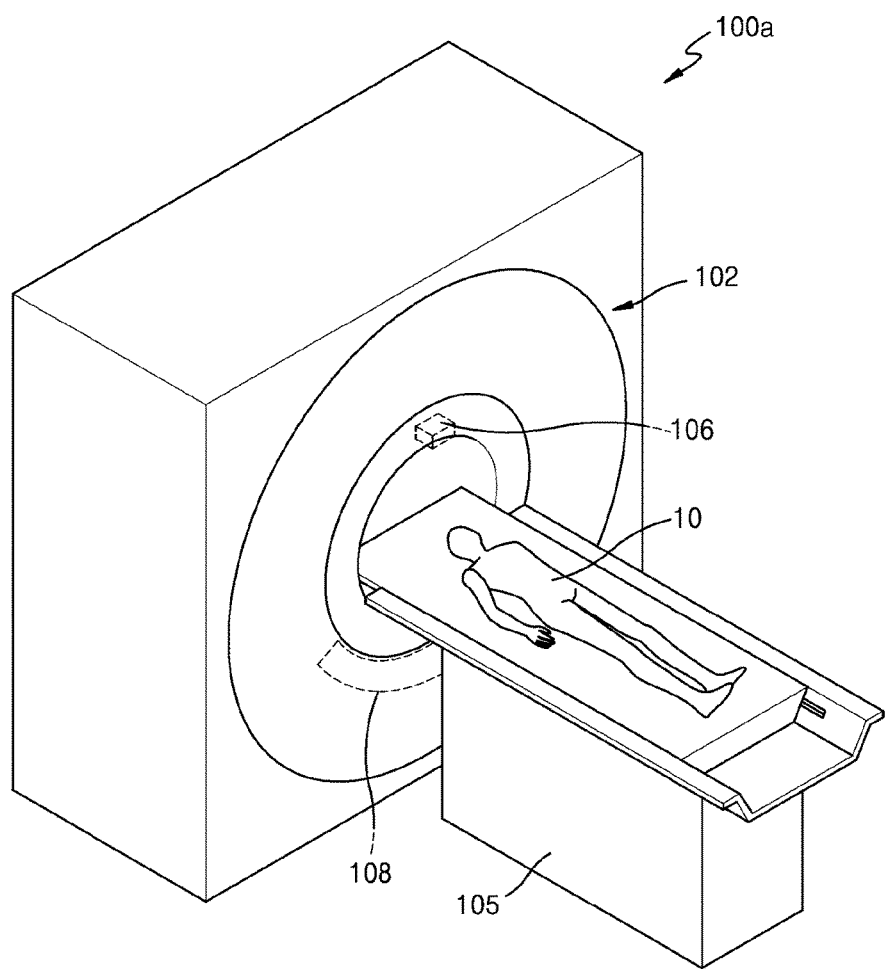
FIG. 1 illustrates a perspective view of a computed tomography (CT) system according to an embodiment.

FIGS. 1 through 26, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged tomography apparatus.

The attached drawings for illustrating exemplary embodiments of the present disclosure are referred to in order to gain a sufficient understanding of the present disclosure, the merits thereof, and the objectives accomplished by the implementation of the present disclosure. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the present disclosure will only be defined by the appended claims Like reference numerals refer to like elements throughout the specification.

The terms used in this specification are those general terms currently widely used in the art in consideration of functions regarding the concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the embodiments means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Reference will now be made in detail to embodiments, examples of which are illustrated in the accompanying drawings. In this regard, the present embodiments may have different forms and should not be construed as being limited to the descriptions set forth herein. In the following description, well-known functions or constructions are not described in detail so as not to obscure the embodiments with unnecessary detail.

Throughout the specification, an "image" may mean multi-dimensional data formed of discrete image elements, e.g., pixels in a two-dimensional (2D) image and voxels in a three-dimensional (3D) image. For example, the image may include a medical image of an object which is captured by a computed tomography (CT) imaging apparatus.

Throughout the specification, a "CT image" may mean an image generated by synthesizing a plurality of X-ray images that are obtained by photographing an object while a CT imaging apparatus rotates around at least one axis with respect to the object.

Throughout the specification, an "object" may include a part of a human or an animal. For example, the object may be an organ (e.g., liver, heart, womb, brain, breast, or abdomen), a blood vessel, or a combination thereof. The object may be a phantom.

Throughout the specification, a "user" may be, but is not limited to, a medical expert including a medical doctor, a nurse, a medical laboratory technologist, a medial image expert, or a technician who repairs a medical apparatus.

According to embodiments, a tomography apparatus may be any imaging apparatus for reconstructing an image by using data obtained by using rays transmitted through an object. Also, a tomography apparatus may be any medical imaging apparatus for reconstructing an image by using projection data obtained by using rays transmitted through an object.

A tomography apparatus according to embodiments may be, for example, a CT apparatus, an optical coherence tomography (OCT) apparatus, or a positron emission tomography (PET)-CT apparatus. A tomography image obtained by a tomography apparatus according to embodiments may be a CT image, a COT image, or a PET image. The following is described on the assumption that a CT image is a tomography image.

Although a CT system is described in embodiments, the scope of the embodiments is not limited thereto and includes various tomography apparatuses.

As used herein, the term "and/or" includes any and all combinations of one or more of the associated listed items. Expressions such as "at least one of," when preceding a list of elements, modify the entire list of elements and do not modify the individual elements of the list.

FIG. 1 illustrates a perspective view of a CT system 100a according to an embodiment. Referring to FIG. 1, the CT system 100a may include a gantry 102, a table 105, an X-ray generator 106, and an X-ray detector 108.

The gantry 102 may include the X-ray generator 106 and the X-ray detector 108.

An object 10 may be placed on the table 105.

The table 105 may move in a predetermined direction (e.g., at least one of up, down, right, and left directions) during a CT imaging procedure. Also, the table 105 may tilt or rotate by a predetermined angle in a predetermined direction.

The gantry 102 may also tilt by a predetermined angle in a predetermined direction.

Figure 2:
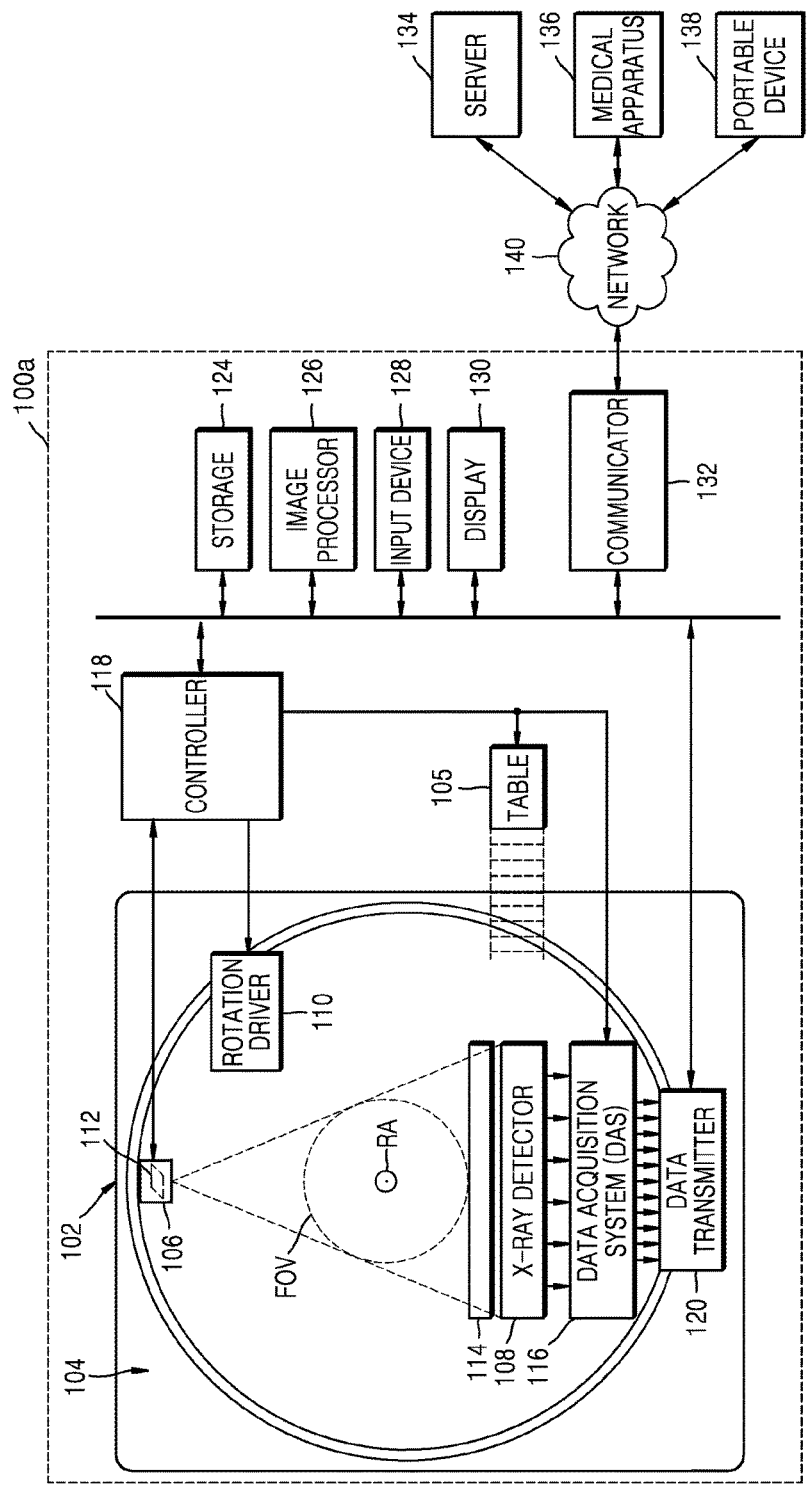
FIG. 2 illustrates a block diagram of a structure of the CT system according to an embodiment.

FIG. 2 illustrates a block diagram of a structure of the CT system 100a. The CT system 100a may include the gantry 102, the table 105, a controller 118, a storage 124, an image processor 126, an input device 128, a display 130, and a communicator 132.

The gantry 102 may include a rotating frame 104, the X-ray generator 106, the X-ray detector 108, a rotation driver 110, a data acquisition system (DAS) 116, and a data transmitter 120.

The rotating frame 104 may include the X-ray generator 106 and the X-ray detector 108 that are arranged to face each other so as to have a predetermined field of view FOV. The rotating frame 104 may also include an anti-scatter grid 114. The anti-scatter grid 114 may be disposed between the X-ray generator 106 and the X-ray detector 108.

In a medical imaging system, X-ray radiation that reaches a detector (or a photosensitive film) includes not only attenuated primary radiation that forms a valuable image but also scattered radiation that deteriorates the quality of an image. The anti-scatter grid may be disposed between a patient and a detector (or a photosensitive film) and may transmit most of primary radiation and may attenuate scattered radiation.

The rotating frame 104 may receive a driving signal from the rotation driver 110 and may rotate the X-ray generator 106 and the X-ray detector 108 at a predetermined rotation speed. The rotating frame 104 may receive the driving signal and power from the rotation driver 110 while the rotating frame 104 contacts the rotation driver 110 via a slip ring (not shown). Also, the rotating frame 104 may receive the driving signal and power from the rotation driver 110 via wireless communication.

The X-ray generator 106 may receive a voltage and current from a power distribution unit (PDU) (not shown) via a slip ring (not shown) and then a high voltage generator (not shown), and may generate and emit X-rays. When the high voltage generator applies a predetermined voltage (hereinafter, referred to as a tube voltage) to the X-ray generator 106, the X-ray generator 106 may generate X-rays having a plurality of energy spectra that correspond to the tube voltage.

The X-ray detector 108 detects radiation. Radiation that reaches the X-ray detector may be X-rays that have been generated by the X-ray generator 106 and have been transmitted through the object 10 and the anti-scatter grid 114. The X-ray detector 108 may include an indirect-type X-ray detector for detecting radiation after converting the radiation into light, and a direct-type X-ray detector for detecting radiation after directly converting the radiation into electric charges. The indirect-type X-ray detector may use a scintillator. Also, the direct-type X-ray detector may use a photon counting detector. The DAS 116 may be connected to the X-ray detector 108. Electrical signals generated by the X-ray detector 108 may be acquired by the DAS 116. Electrical signals generated by the X-ray detector 108 may be acquired by wire or wirelessly by the DAS 116. Also, the electrical signals generated by the X-ray detector 108 may be provided to an analog-to-digital converter (not shown) via an amplifier (not shown).

According to a slice thickness or the number of slices, only some of a plurality of pieces of data collected by the X-ray detector 108 may be provided to the image processor 126 via the data transmitter 120, or the image processor 126 may select only some of the plurality of pieces of data.

Such a digital signal may be provided to the image processor 126 via the data transmitter 120. The digital signal may be provided to the image processor 126 by wire or wirelessly.

The controller 118 may control an operation of each of the elements in the CT system 100a. For example, the controller 118 may control operations of the table 105, the rotation driver 110, the collimator 112, the DAS 116, the storage 124, the image processor 126, the input device 128, the display 130, the communicator 132, and the like. A plurality of the controllers 118 may be provided, and may receive a control signal from an external apparatus and may control an operation of the CT system 100a.

The image processor 126 may receive data acquired by the DAS 116 (e.g., pure data that is data before processing), via the data transmitter 120, and may perform pre-processing.

The pre-processing may include, for example, a process of correcting a sensitivity irregularity between channels and a process of correcting signal loss due to a rapid decrease in signal strength or due to the presence of an X-ray absorbing material such as metal.

Data output from the image processor 126 may be referred to as raw data or projection data. The projection data may be stored in the storage 124 with imaging conditions (e.g., the tube voltage, an imaging angle, etc.) during the acquisition of data.

The projection data may be a group of data values that correspond to the intensity of the X-rays that have passed through the object 10. For convenience of description, a group of a plurality of pieces of projection data that are simultaneously obtained from all channels at the same imaging angle is referred to as a projection data set.

The storage 124 may include a volatile or non-volatile storage medium.

The input device 128 may include a device for receiving a predetermined input from an external source. The input device 128 may receive an external input with respect to an X-ray tomography imaging condition, an image processing condition, or the like.

The display 130 may display an X-ray image reconstructed by the image processor 126.

Exchanges of data, power, or the like between the aforementioned elements may be performed by using at least one of wired communication, wireless communication, and optical communication.

The communicator 132 may communicate with an external device or an external medical apparatus. The communicator 132 may be wiredly or wirelessly connected to a network 140 and therefore may communicate with a server 134, an external medical apparatus 136, or a portable device 138. The communicator 132 may exchange data with a hospital server or another medical apparatus in a hospital, which is connected thereto via a PACS.

Also, the communicator 132 may perform data communication with the portable device 138 or the like, according to the digital imaging and communications in medicine (DICOM) standard.

The communicator 132 may transmit and receive data related to diagnosing the object 10, via the network 140. Also, the communicator 132 may transmit and receive a medical image obtained from the medical apparatus 136 such as a magnetic resonance imaging (MRI) apparatus, an X-ray apparatus, or the like.

Furthermore, the communicator 132 may receive a diagnosis history or a medical treatment schedule about a patient from the server 134 and may use the diagnosis history or the medical treatment schedule to diagnose the patient. Also, the communicator 132 may perform data communication not only with the server 134 or the medical apparatus 136 in a hospital but also with the portable device 138 of a user or patient.

Also, the communicator 132 may transmit information about a device error, information about a quality control status, or the like to a system manager or a service manager via the network 140, and may receive a feedback regarding the information from the system manager or service manager.

At least one of the server 134, the medical apparatus 136, and the portable device 138 may transmit a tomography control signal to the CT system 100a through the network 140. The term "control signal" used herein may refer to a signal for controlling at least one operation from among an operation of performing a tomography scan, an operation of obtaining raw data, an operation of reconstructing a tomography image, and an operation of transmitting/receiving raw data or a tomography image.

In detail, the CT system 100a may perform at least one operation from among an operation of performing a tomography scan, an operation of obtaining raw data, an operation of reconstructing a tomography image, and an operation of transmitting/receiving raw data or a tomography image, based on a control signal transmitted from at least one of the server 134, the medical apparatus 136, and the portable device 138.

Figure 3A:
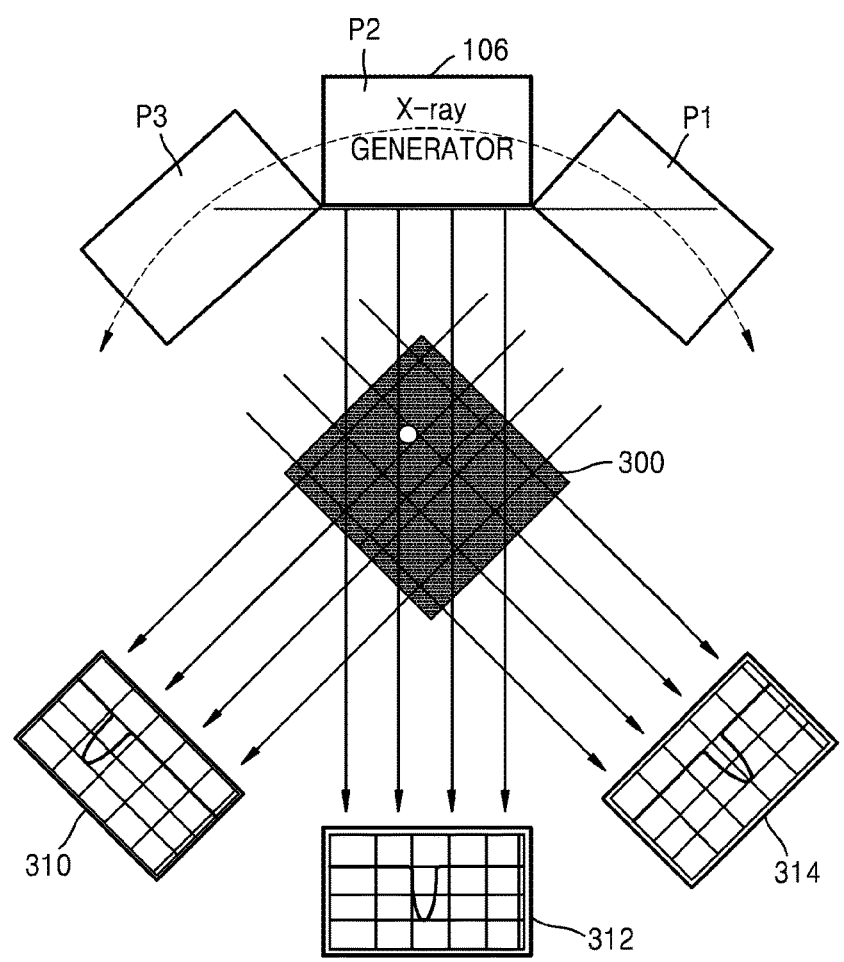
FIGS. 3A and 3B illustrate views for explaining a process of obtaining and reconstructing a tomography image according to an embodiment.
Figure 3B:
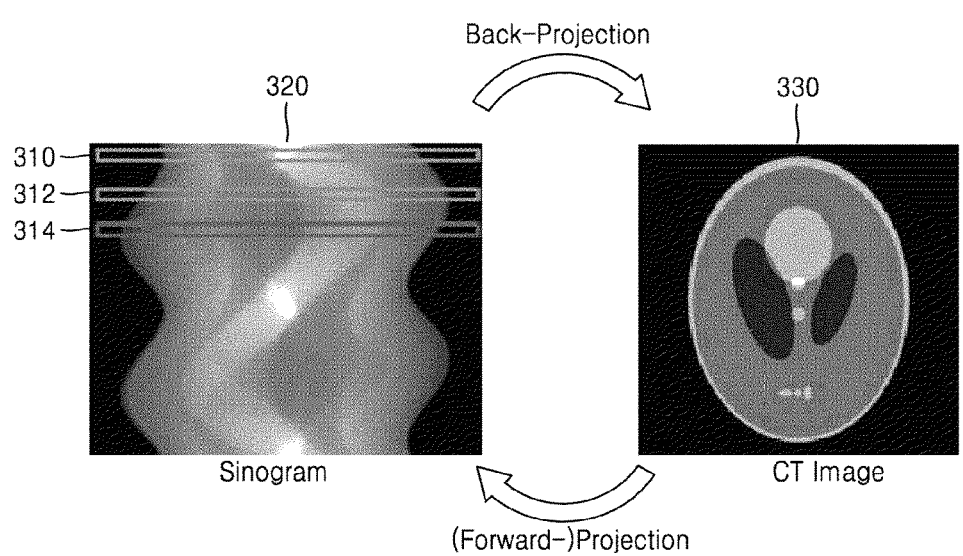

FIGS. 3A and 3B illustrate views for explaining a process of obtaining and reconstructing a tomography image according to an embodiment. In detail, FIG. 3A is a view for explaining an imaging operation of the CT system 100a for performing a tomography scan by rotating around an object 300 and obtaining raw data. FIG. 3B is a view for explaining a sinogram 320 and a tomography image 330 obtained by the CT system 100a.

For example, the CT system 100a may provide a relatively accurate cross-sectional image of an object by obtaining and processing image data corresponding to an object body part having a thickness equal to or less than 2 mm tens to hundreds of times per second. Although a conventional method has a problem in that only a horizontal-sectional image may be expressed, the problem has been solved by developing various methods of reconstructing images. Examples of a method of reconstructing a 3D image include shade surface display (SSD), maximum intensity projection (MIP)/minimum intensity projection (MinIP), volume rendering (VR), virtual endoscopy, multi-planar reformation (MPR), editing, and voxel of interest (VOI).

The CT system 100a obtains raw data by performing a tomography scan on an object in order to obtain the tomography image 330. The CT system 100a reconstructs the tomography image 330 by using the obtained raw data. The term 'reconstruction' used herein may be referred to as 'restoration'. The term 'raw data' may refer to projection data obtained by emitting X-rays to the object or the sinogram 320 that is a set of projection data. When an image is reconstructed, it means that a tomography image is generated from raw data. Filtered back-projection may be performed in a process of reconstructing an image.

Once the sinogram 320 is obtained as raw data, the CT system 100a performs image reconstruction by using the sinogram 320 in order to obtain the tomography image 330.

The CT system 100a generates and emits X-rays to the object and detects the X-rays having passed through the object by using the X-ray detector 108. The X-ray detector 108 generates raw data corresponding to the detected X-rays.

In detail, referring to FIG. 3A, the X-ray generator 106 included in the CT system 10a emits X-rays to the object 300. The X-ray generator 106 rotates around the object 300 and obtained a plurality of pieces of raw data corresponding to rotation angles. In detail, the CT system 100a obtains first raw data 310 by detecting X-rays applied to the object 300 at a position P1 and obtains second raw data 312 by detecting X-rays applied to the object 300 at a position P2. The CT system 100a obtains third raw data 314 by detecting X-rays applied to the object 300 at a position P3. Each raw data may be projection data. Also, the raw data may be a sinogram that is a set of projection data.

In order to generate one tomography image, the X-ray generator 106 has to perform a CT scan by rotating by at least 180°.

Referring to FIG. 3B, the CT system 100a may obtain one sinogram 320 by combining a plurality of pieces of projection data, that is, the first through third raw data 310, 312, and 314, obtained by moving the X-ray generator 106 at predetermined angular intervals as described with reference to FIG. 3A. The sinogram 320 of FIG. 3B is a sinogram obtained when the X-ray generator 106 rotates by one cycle and performs a CT scan. The sinogram 320 corresponding to one cycle rotation may be used to generate one tomography image 330. One cycle rotation may be about a half turn or one full rotation or more according to a type of the CT system 100a.

The CT system 100a reconstructs the tomography image 330 by filtering the sinogram 320 and then performing filtered back-projection.

As described above, the CT system 100a obtains a tomography image by performing imaging including one cycle rotation. When an object that moves is imaged, motion of the object may occur even during one cycle rotation. For example, about 0.2 seconds may be taken for the X-ray generator 106 to rotate a half round and motion of the object may occur in the 0.2 seconds. Due to the motion of the object in one cycle, motion artifacts and skewness may occur when a tomography image is reconstructed.

Figure 4:
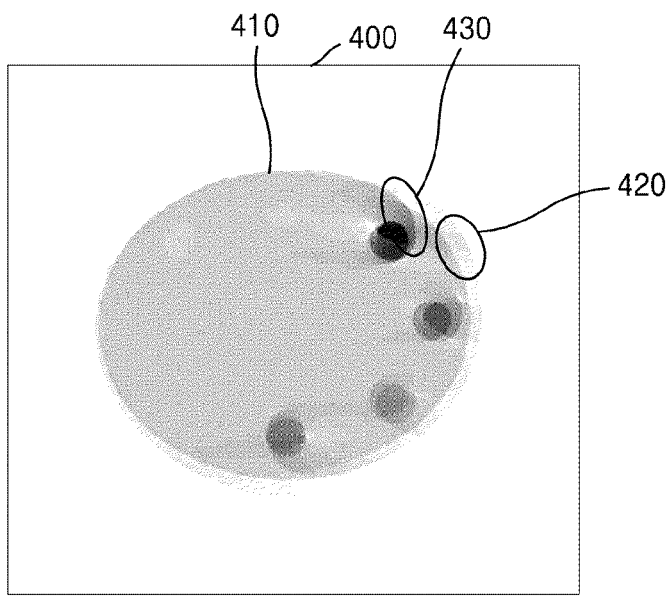
FIG. 4 illustrates a view for explaining motion artifacts occurring in a reconstructed CT image.

FIG. 4 illustrates a view for explaining motion artifacts occurring in a reconstructed CT image. FIG. 4 illustrates a CT image obtained by using a full reconstruction method of reconstructing an image by using raw data that is obtained by rotating around an object 360° or more.

Referring to FIG. 4, when motion artifacts occur, an outermost edge 420 of an object 410 in a reconstructed CT image 400 is unclear and overlaps itself or others, and an inner edge 430 is blurred due to motion of the object 410.

The motion artifacts in the reconstructed CT image 400 reduce the quality of the reconstructed CT image 400, and when a user, for example, a doctor, reads the reconstructed CT image 400 and diagnoses a disease, the user is unable to accurately read the reconstructed CT image 400 and diagnose the disease.

Figure 5:
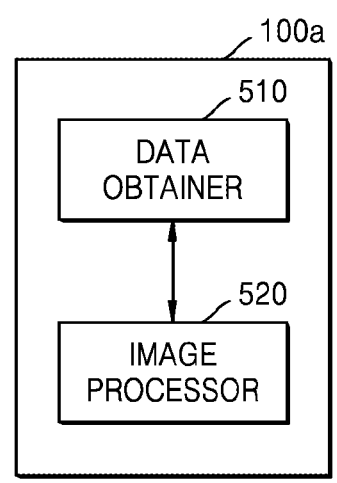
FIG. 5 illustrates a structure of a tomography apparatus according to an embodiment.

FIG. 5 illustrates a structure of a tomography apparatus 100b according to an embodiment.

The tomography apparatus 100b according to an embodiment includes a data obtainer 510 and an image processor 520. The tomography apparatus 100b may be any electronic apparatus for reconstructing a tomography image by using raw data obtained by performing a tomography scan.

In detail, the tomography apparatus 100b according to an embodiment may be included in the CT system 100a of FIGS. 1 and 2. Also, the tomography apparatus 100b may be included in the server 134, the medical apparatus 136, or the portable device 138 of FIG. 2, and may be connected to the CT system 100a. When the tomography apparatus 100b is included in the CT system 100a of FIG. 1, the data obtainer 510 and the image processor 520 of FIG. 5 may be included in the image processor 126 of FIG. 2. Alternatively, the data obtainer 510 and the image processor 520 may correspond to at least one element included in the gantry 102 and the image processor 126 of FIG. 2.

The data obtainer 510 performs a tomography scan on an object and obtains raw data for the object. According to an embodiment, the data obtainer 510 may correspond to the gantry 102 of FIG. 1. In detail, the data obtainer 510 may include the X-ray generator 106, the X-ray detector 108, the rotation driver 110, the DAS, and the table 105.

Also, when the data obtainer 510 is connected to the CT system 100a, the data obtainer 510 may receive raw data obtained by performing a tomography scan from the CT system 100a that is connected to the data obtainer 510.

The object that is an organ of a moving body may include at least one of, for example, the heart, blood vessels, the lung, the bronchus, or the midriff. The object in the tomography image may be expressed by at least one of a surface and an edge. Also, even when a surface or an edge of the object is not clear, the object may be expressed by a brightness value difference in the tomography image. For example, one or more tissues of the heart may be expressed to have different brightness values in the tomography image, or a surface of each tissue may be expressed in the tomography image.

According to an embodiment, the object may be an object that moves periodically. For example, the object may be the heart and may move periodically. In the specification, a time in a motion cycle of the object is referred to as a 'phase'. The phase may be expressed in a percentage (%) or the like indicating a time or an elapsed time to a total cycle according to an embodiment.

According to an embodiment, the data obtainer 510 may rotate around the object and may obtain raw data by performing a tomography scan. The raw data may be projection data obtained by emitting radiation to the object or a sinogram that is a set of projection data. When the X-ray generator 106 emits X-rays to the object at a predetermined position, a viewpoint or a direction in which the X-ray generator 106 faces the object is referred to as a view. Projection data refers to raw data obtained to correspond to one view, and a sinogram refers to raw data obtained by sequentially arranging a plurality of pieces of projection data.

According to an embodiment, the data obtainer 510 may perform a tomography scan so that the X-ray generator 106 rotates around the object about a z-axis of the object and helically travels in a z-axis direction. For example, the z-axis of the object may be a central axis of the body of the object.

The image processor 520 reconstructs a first tomography image of the object from the raw data. In detail, the image processor 520 reconstructs a first tomography image of the object for a first slice section in a first phase. The first tomography image is a tomography image indicating a state in the first phase for the first slice section of the object. The slice section may be referred to as a volume. Also, the image processor 520 reconstructs a second tomography image of the object for the first slice section in a second phase that is different from the first phase by applying 3D motion information of the object to the raw data. The image processor 520 may reconstruct the second tomography image in the second phase by using the 3D motion information of the object in filtered back-projection. According to an embodiment, after the data obtainer 510 obtains the raw data and reconstructs the first tomography image, the image processor 520 may reconstruct the second tomography image of the object in the second phase, which is different from the first phase, by using the first tomography image and the 3D motion information of the object.

The second phase may be a phase beyond a reconstructable range from the raw data for the first slice section. When an object that moves is scanned, a slice section and a phase of the object vary as time passes. Accordingly, a reconstructable phase range for each slice section from raw data may be different. The term 'reconstructable phase range' refers to a phase range in which reconstruction may be performed by using a reconstruction method used by the tomography apparatus 100b. For example, when a tomography image in a phase of about 30% to about 40% may be restored from the raw data for the first slice section, the second phase may be 70%.

According to an embodiment, when the tomography apparatus 100b uses a half reconstruction method, a phase range in which raw data exists and that corresponds 180°+ fan angle from a position of the X-ray generator 106 where imaging is performed in a certain phase is a reconstructable phase range. When raw data exists, it means that a motion artifact-free reconstructable range is included.

Alternatively, when the tomography apparatus 100b uses a full reconstruction method, a phase range in which raw data exists and corresponds to 360° from a position of the X-ray generator 106 where imaging is performed in a certain phase is a reconstructable phase range.

Figure 6:
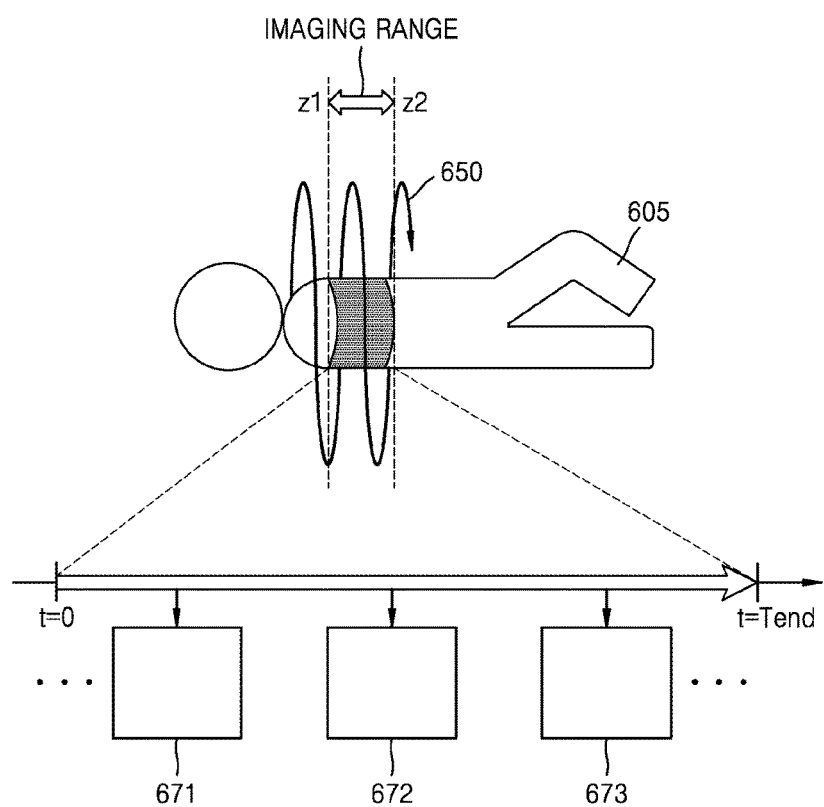
FIG. 6 illustrates a view for explaining a tomography scan using a helical scan method according to an embodiment.

FIG. 6 illustrates a view for explaining a tomography scan using a helical scan method according to an embodiment.

A helical scan method is a tomography scan method of performing imaging so that an X-ray source helically travels for a period of time from t=0 to t=end. That is, the X-ray generator 106 may perform a tomography scan by moving along a helical trajectory 650. A method of performing a tomography scan by using a helical scan method is referred to as a 'helical imaging method'.

The data obtainer 510 according to an embodiment may perform helical imaging by emitting X-rays in a set imaging range at a set pitch, irrespective of a cycle of motion of an object. The term 'pitch' which is a value indicating a speed of the X-ray generator 106 refers to a movement distance of the table 105 in the z-axis direction while the X-ray generator 106 rotates 360°.

The imaging range may be automatically set to a range in which the object is within an FOV or may be set by a user. For example, as shown in FIG. 6, the imaging range may set to a range from z1 to z2 in which the heart that is a moving object is located.

According to an embodiment, a pitch of the X-ray generator 106 may be set to a maximum pitch at which a tomography image may be reconstructed in a reconstruction method used by the image processor 520. The image processor 520 may use a half reconstruction method or a full reconstruction method.

When a light source of the X-ray generator 106 uses a cone beam having a cone shape and uses a half reconstruction method, a pitch may be set to obtain raw data corresponding to a minimum angle (180°+fan angle) for each tomogram. That is, when the X-ray generator 106 rotates at a constant speed, a pitch may be a value corresponding to a movement distance of the table 105 in the z-axis direction during a rotation by 360°.

When a parallel beam is used and a half reconstruction method is used, a pitch may be set so that raw data corresponding to a minimum angle of 180° is obtained for each tomogram. That is, when the X-ray generator 106 rotates at a constant speed, a pitch may be a value corresponding to a movement distance of the table 105 in the z-axis direction during a rotation by a minimum angle of 180°.

When a parallel beam is used so that light output as a cone beam of the X-ray generator 106 is emitted in parallel to the object and a full reconstruction method is used, a pitch may be set so that raw data corresponding to 360° is obtained for each tomogram. That is, when the X-ray generator 106 rotates at a constant speed, a pitch may be a value corresponding to a movement distance of the table 105 in the z-axis direction during a rotation by 360°. A cone beam and a parallel beam will be explained below in detail with reference to FIG. 9.

While imaging is performed by using a helical imaging method, a plurality of tomography images 671, 672, and 673 that are cross-sectional images of the object at different positions may be obtained. The tomography images 671, 672, and 673 obtained at the different positions have a tomography scan time difference therebetween.

Figure 7:
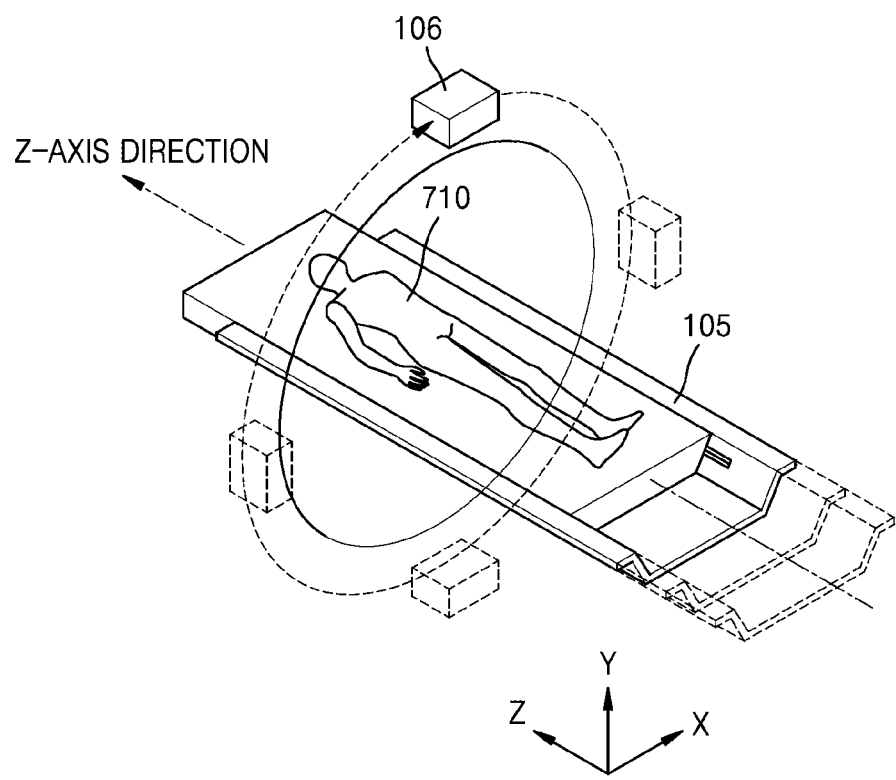
FIG. 7 illustrates a view for explaining a helical scan method according to an embodiment.

FIG. 7 is a view for explaining a helical scan method according to an embodiment.

According to an embodiment, the data obtainer 510 performs a helical scan by rotating the X-ray generator 106 about the z-axis and moving the table 105 so that an object 710 is moved in the z-axis direction. When the object 710 is placed on the table 105, the data obtainer 510 may move the object 710 in the z-axis direction by moving the table 105 at a constant speed in the z-axis direction. A movement speed of the X-ray generator 106 and a movement speed of the table 105 may be adjusted according to a set pitch.

Figure 8:
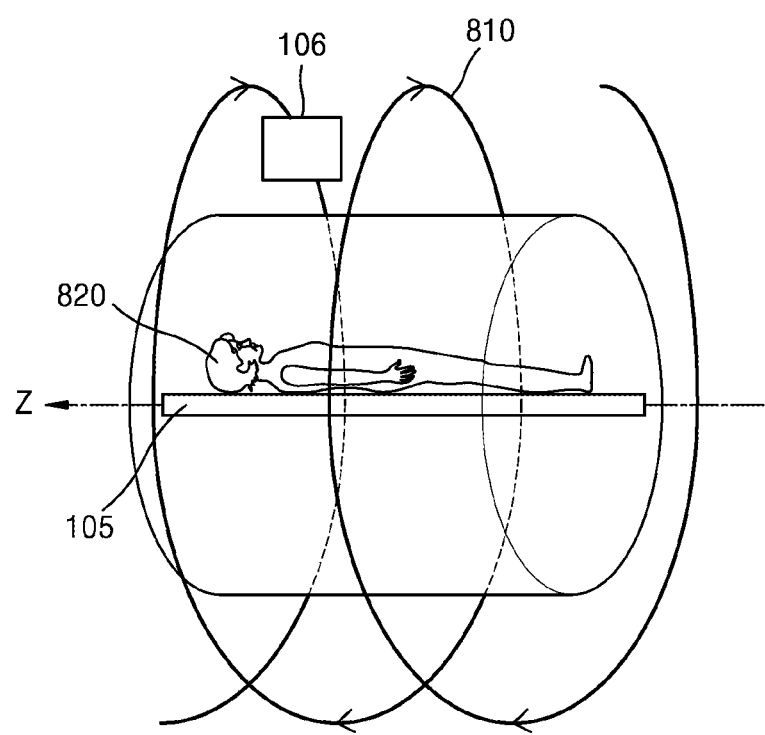
FIG. 8 illustrates a view for explaining a helical scan method according to an embodiment.

FIG. 8 illustrates a view for explaining a helical scan method according to an embodiment.

According to an embodiment, the data obtainer 510 may perform a helical scan by moving the X-ray generator 106 along a helical trajectory 810, without moving an object 820. For example, when the object 820 is placed on the table 105, the data obtainer 510 may locate the table 105 at a predetermined position in a gantry and may move the X-ray generator 106 along the helical trajectory 810 in the gantry. A movement speed of the X-ray generator 106 and the helical trajectory 810 may be adjusted according to a set pitch.

Figure 9A:
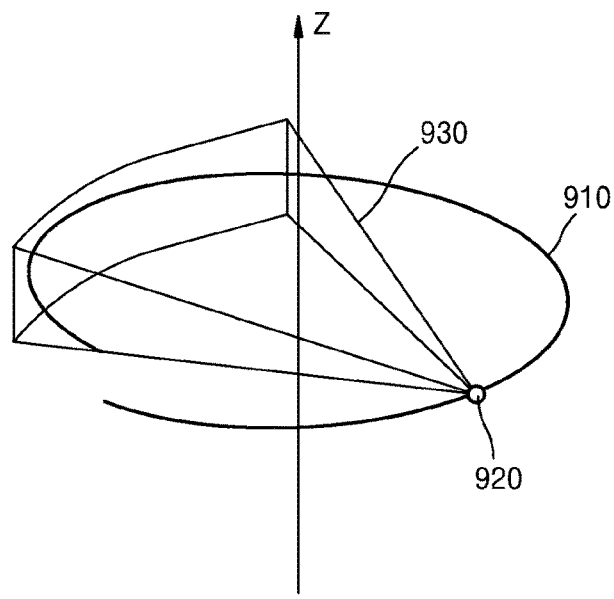
FIGS. 9A and 9B illustrate views for explaining a case where an X-ray generator generates a cone beam and a case where the X-ray generator generates a parallel beam according to an embodiment.
Figure 9B:
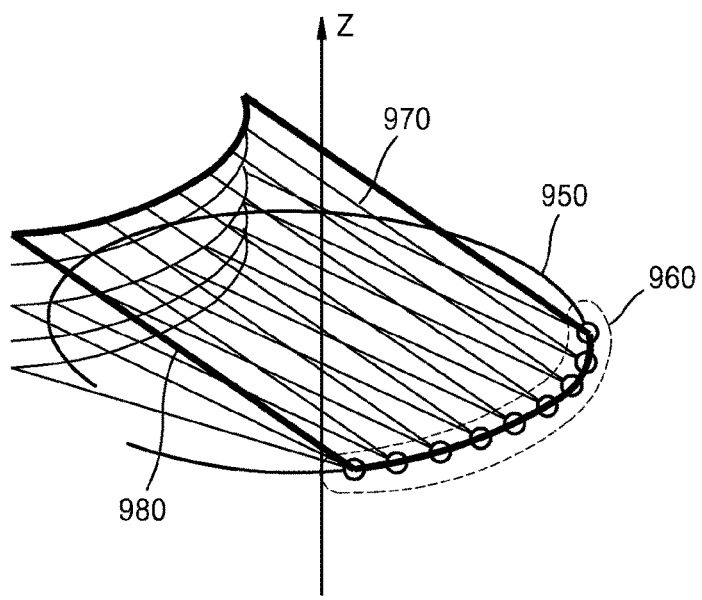

FIGS. 9A and 9B illustrate views for explaining a case where the X-ray generator 106 generates a cone beam and a case where the X-ray generator 106 generates a parallel beam according to an embodiment.

According to an embodiment, as shown in FIG. 9A, when the X-ray generator 106 emits X-rays at a predetermined position 920 while moving along a trajectory 910, X-rays having a cone shape 930 are emitted to an object. The X-rays having the cone shape 930 are referred to as a cone beam.

According to another embodiment, as shown in FIG. 9B, when the X-ray generator 106 emits X-rays at a predetermined position 960 while moving along a trajectory 950, X-rays having a parallel plane shape 970 are emitted to the object. The X-rays having the parallel plane shape 970 are referred to as a parallel beam.

Referring to FIG. 9B, when the X-ray generator 106 emits X-rays as a cone beam, the cone beam may be rearranged to be parallel on a plane 980 that connects a row of the X-ray detector 108 and a trajectory of the beam. That is, the tomography apparatus 100b may convert a cone beam into a pseudo parallel beam and may use the pseudo parallel beam. Also, unlike in a case where the X-ray generator 106 generates a parallel beam, when the X-ray generator 106 converts a cone beam into a parallel beam and uses the parallel beam, raw data has to be obtained by further rotating by a fan angle 'a'. In detail, when the fan angle is 'a', raw data corresponding to an angular section of 180+a corresponding to a rebinned parallel beam may be obtained by using raw data obtained in an angular section of 180+2a by the X-ray generator 106 that emits a cone beam.

A tomography apparatus according to embodiments may be applied to a CT apparatus for emitting a cone beam or a CT apparatus for emitting a parallel beam.

Figure 10:
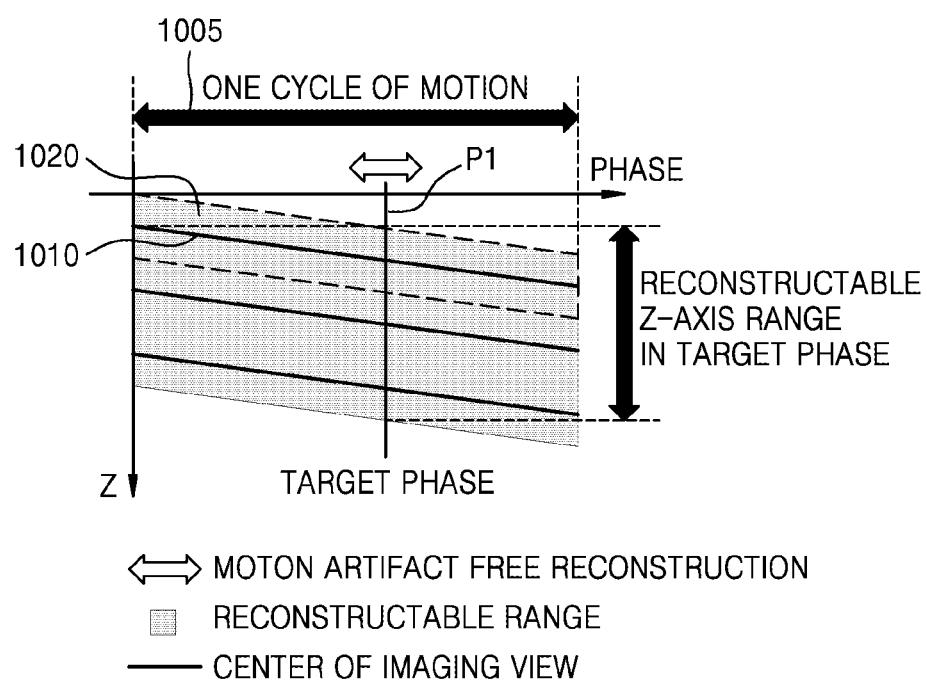
FIG. 10 illustrates a view for explaining a helical imaging method at a low pitch.

FIG. 10 illustrates a view for explaining a helical imaging method at a low pitch.

When a helical heart CT scan is performed, a reconstructable target phase in each slice section is limited. A size of a reconstructable phase range is determined according to a heart rate of a patient, a movement speed of a table, and a FOV of a reconstructed image, and the table needs to move at a low pitch in order to obtain a reconstructed image for all desired body parts.

In FIG. 10, a z-axis is a movement direction of the table 105 or the X-ray generator 106, and an axis perpendicular to the z-axis represents a 'phase'. Also, a solid line 1010 indicates the center of an imaging view of the X-ray generator 106, and a block 1020 indicates a range in which a tomography image may be reconstructed from raw data obtained when X-rays emitted by the X-ray generator 106 pass through an object.

The image processor 520 may reconstruct a tomography image of the object in a target phase P1 by using raw data. The target phase P1 may correspond to a predetermined position in one cycle 1005 of motion.

When imaging is performed at a low pitch in the tomography apparatus 100b as shown in FIG. 10, raw data is continuously accumulated in a z-axis direction. Accordingly, a tomography image may be reconstructed without discontinuity in the z-axis in the predetermined target phase. However, when imaging is performed at a low pitch, an imaging time is increased, a radiation dose to the patient is increased, and inconvenience which the patient feels due to the increased imaging time is increased. In addition, when a heart rate of the patient becomes irregular, there is a risk of generating a slice that may not be reconstructed in a desired phase, thereby causing discontinuity between slices of a reconstructed image.

Figure 11:
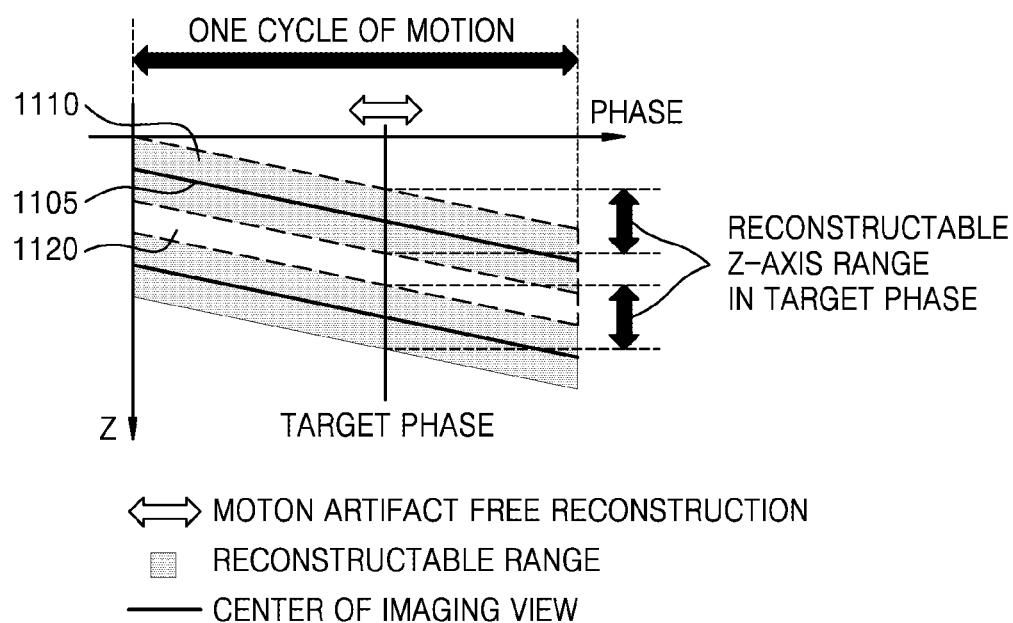
FIG. 11 illustrates a view for explaining a helical imaging method at a high pitch.

FIG. 11 illustrates a view for explaining a helical imaging method at a high pitch.

In FIG. 11, a solid line 1105 indicates the center of an imaging view of the X-ray generator 106, a block 1110 indicates a range in which a tomography image may be reconstructed from raw data obtained when X-rays emitted by the X-ray generator 106 pass through an object, and a block 1120 indicates a range in which a tomography image may not be reconstructed.

When imaging is performed at a high pitch in the tomography apparatus 100b as shown in FIG. 11, an imaging time may be reduced. However, when imaging is performed at a high pitch, since a section in which raw data is not obtained occurs as shown in the block 1120, a reconstructed image for all slice sections may not be obtained. In particular, when an image of the same region in a plurality of target phases is to be obtained, for example, in a four dimensional (4D) scan, since a reconstructable range varies according to each target phase, a pitch has to be sufficiently reduced in order to compare reconstructed images of the same region in different phases, and thus there is a limitation in reducing an imaging time.

In particular, when the heart is imaged, since a reconstructed image that allows easy diagnosis may be obtained only in some phases of diastole or systole with a relatively small amount of motion, in order to obtain a reconstructed image of the entire heart including a z-axis range, imaging needs to be performed at a lower pitch than that used to image other body parts. An imaging range in which easy diagnosis is allowed varies according to a heart rate of a patient. In particular, when the patient has a high heart rate, in order to obtain a reconstructed image of one slice section, two or more heartbeats have to be used (e.g., multi-segment reconstruction has to be used), thereby further reducing a pitch of imaging and increasing an imaging time.

When the patient has a low heart rate or a heart rate is intentionally reduced by using a drug such as β-blocker, in order to reconstruct a tomography mage including the entire heart (which has a size of about 16 cm) in a general system condition excluding some systems having a very wide detection range, it is necessary to obtain an image for two or more heartbeats, thereby increasing a radiation dose to the patient, increasing an imaging time, and increasing patient inconvenience.

In a general reconstruction method, one image may be obtained after one used for reconstruction is selected from among all phases, and it may be considered a reconstructed value in a phase (i.e., a target phase) corresponding to the center of a selected image. In particular, in order to obtain a reconstructed image having quality high enough to make a diagnosis, only an image that is captured when the amount of motion of the heart is small may be used, and a range corresponding to the image is determined depending on beats of the patient per minute.

Figure 12A:
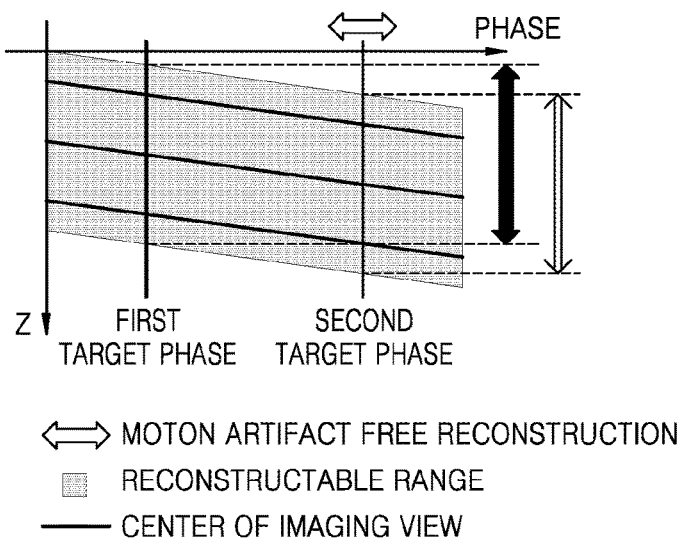
FIGS. 12A and 12B illustrate views for explaining a process of reconstructing a slice, FIG. 12A illustrating a case where imaging is performed at a low pitch, FIG. 12B illustrating a case where imaging is performed at a high pitch.
Figure 12B:
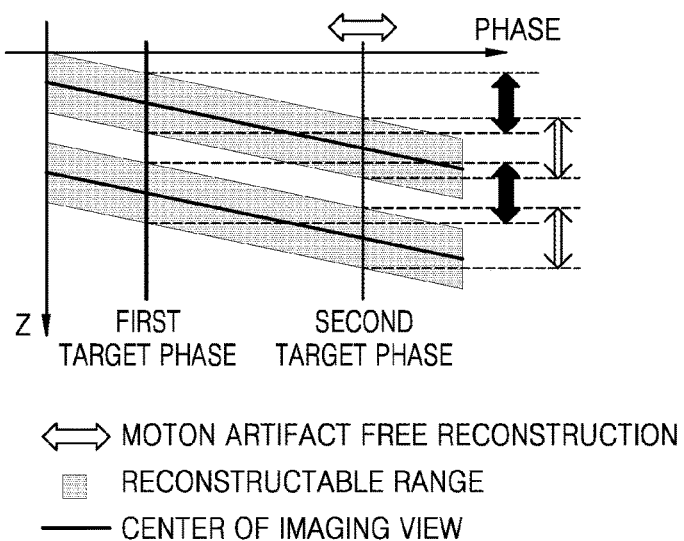

FIGS. 12A and 12B illustrate views for explaining a process of reconstructing a slice. FIG. 12A illustrates a case where imaging is performed at a low pitch. FIG. 12B illustrates a case where imaging is performed at a high pitch.

In an existing heart CT scan, since a reconstructable slice range that may be obtained in a limited target phase varies according to a pitch, in order to obtain an image for all slice sections, imaging needs to be performed at a low pitch as shown in FIG. 12A. If a reconstructed image of a desired slice section is to be obtained at a high pitch, the reconstructed image has different target phases according to slices as shown in FIG. 12B. When various pieces of phase information are included in a reconstructed image, skewness may occur in the reconstructed image.

Figure 13A:
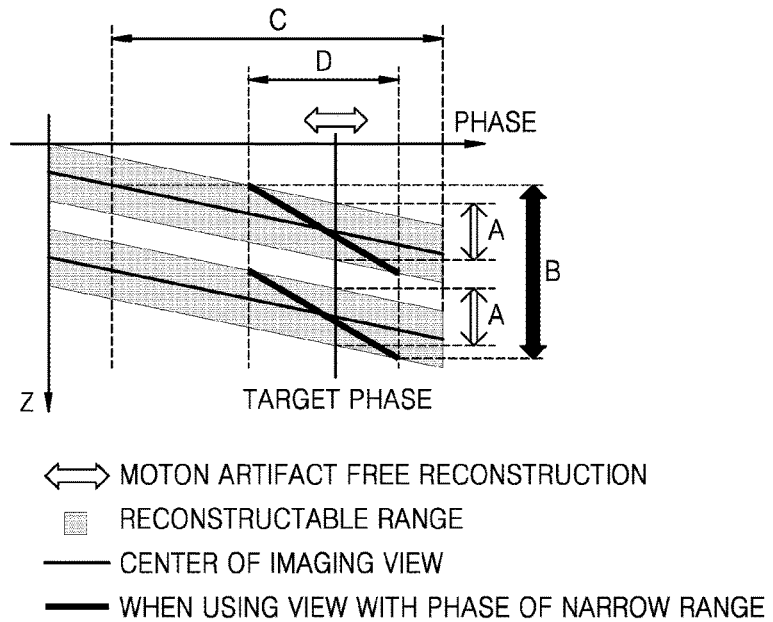
FIGS. 13A and 13B illustrate views for explaining reconstruction of a slice and skewness of an image.
Figure 13B:
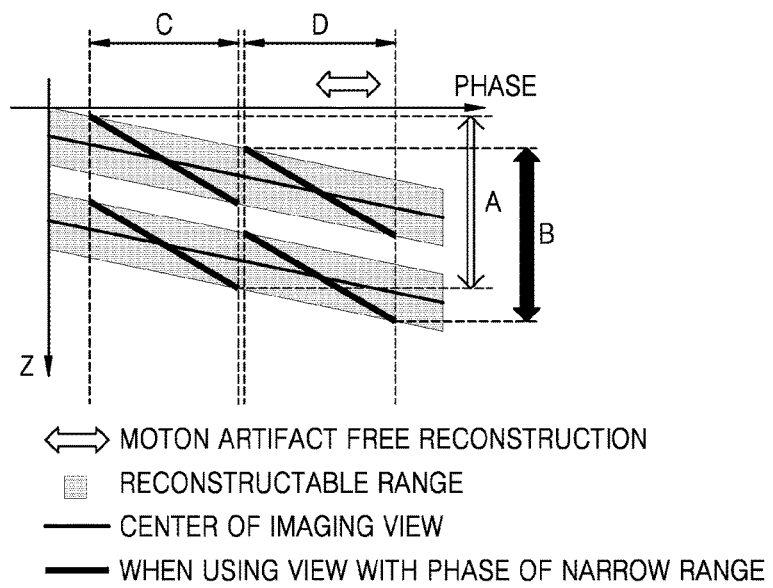

FIGS. 13A and 13B illustrate views for explaining reconstruction of a slice and skewness of an image.

Referring to FIG. 13A, when reconstruction of a slice in a wide range (e.g., a B range) compared to a pitch is performed, since a phase is determined based on a view corresponding to the center of each imaged slice in a wide phase range (e.g., a C phase range), skewness is high. However, the skewness may be minimized by adjusting a projection view and a target phase used for reconstruction in each slice section (e.g., a D phase range).

Referring to FIG. 13B, as a reconstructed image of a wide slice section is included in a narrow phase range, a reconstructed image in various phases (e.g., a C phase range and a D phase range) may be obtained as shown in FIG. 13B, and an image may be stably reconstructed for all slice sections by using a motion correction reconstruction method.

Accordingly, 4D reconstruction (reconstruction in various phases) that was possible only in imaging for many heartbeats at a very low pitch is possible in imaging at a relatively high pitch. In this case, a tomography image in various phases may be obtained even in heart imaging for one cycle by adjusting a pitch as shown in FIG. 13B.

Figure 14:
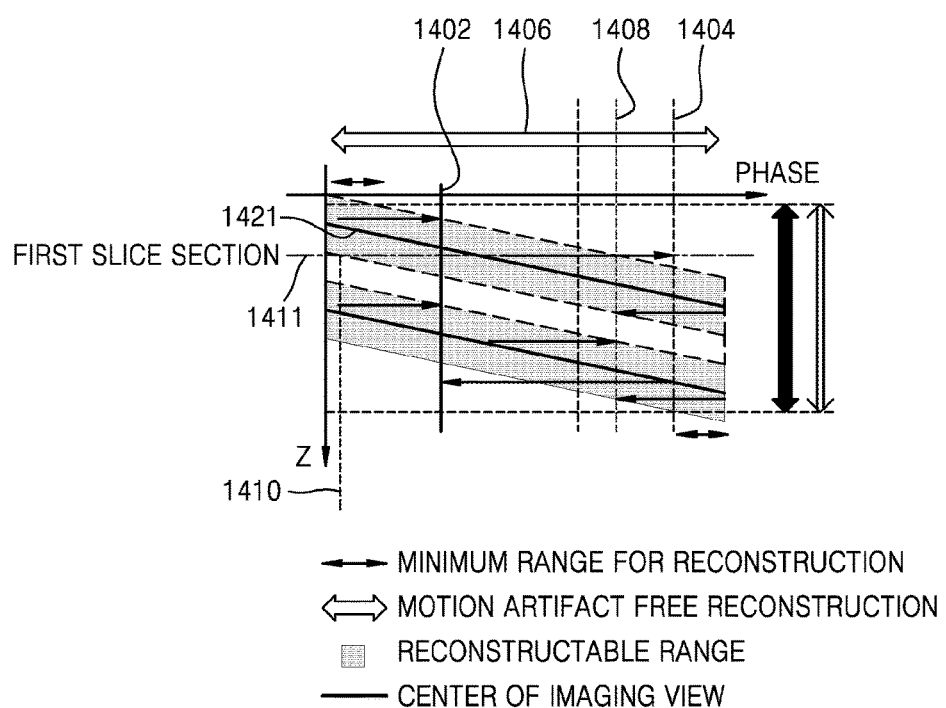
FIG. 14 illustrates a view for explaining a process of reconstructing a tomography image according to an embodiment.

FIG. 14 illustrates a view for explaining a process of reconstructing a tomography image according to an embodiment.

According to an embodiment, then image processor 520 reconstructs a tomography image of an object in a second phase, which is beyond a reconstructable phase range, from raw data by using 3D motion information of the object. Since the object periodically moves, the object has a repeated motion pattern. Accordingly, the image processor 520 may reconstruct a tomography image in a phase beyond a reconstructable phase range from raw data by using motion information that is information about a repeated motion pattern.

Referring to FIG. 14, the image processor 520 may reconstruct a first slice section 1411 corresponding to a first imaging phase 1402 from raw data, may reconstruct a first tomography image of the object from the first imaging phase 1402 corresponding to the first slice section 1411, may obtain motion information for converting a phase into a second target phase 1404 from the first imaging phase 1402, and may reconstruct a second tomography image of the second target phase 1404 by applying the obtained motion information to the raw data.

The first imaging phase 1402 is determined by a phase in which the first slice section 1411 is imaged. According to an embodiment, when a tomography image is reconstructed with data of the center of an imaging view, the first imaging phase 1402 indicates a phase at an intersection between a position of the first slice section 1411 on a z-axis and a line 1421 indicating the center of the imaging view. According to another embodiment, a phase 1408 having a smallest phase difference from a first target phase in a reconstructable range (between 1410 and 1408 of FIG. 14) corresponding to the position of the first slice section 1411 on the z-axis may be determined as the first imaging phase. The reconstructable range corresponding to the position on the z-axis may be defined as a phase range in which a line indicating the position of the first slice section 1411 on the z-axis and a reconstructable section overlap each other.

According to an embodiment, the image processor 520 reconstructs a tomography image in a target phase beyond a reconstructable phase range of raw data by predicting a motion state of the object in a target phase based on motion information and applying a motion correction value to the raw data obtained by imaging based on the predicted motion state.

3D motion information of the object may indicate a motion direction of a surface of the object. In detail, motion information that is 3D motion information of the object as time passes may indicate motion of a surface of the object as time passes. Also, motion information may be information indicating motion of the object for one cycle of motion described with reference to FIGS. 10 and 11, or may be information indicating motion of the object for a period of time equal to or greater than one cycle of motion. 3D motion information includes 3D motion information over a plurality of slices of raw data. Hereinafter, for convenience of explanation, 3D motion information of the object is referred to as 'motion information'. Motion information may be obtained by using a method of reconstructing images after imaging an object at conjugate angles and comparing the images, a method using a motion model of the object, a method of repeatedly performing back-projection and forward-projection on raw data, a method of using a user input, or a combination thereof.

A process of obtaining a motion correction value from the first imaging phase to the first target phase may vary according to a type of the motion information. When the motion information is expressed as a function according to a phase or a time according to an embodiment, the image processor 520 may determine the motion correction value by using sigma summation or the integration of a motion information function in the first target phase range from the first imaging phase. According to an embodiment, when there is motion information in non-continuous phases, the image processor 520 may obtain the motion correction value by using an interpolation method. Linear interpolation and non-linear interpolation may be used as the interpolation method according to an embodiment.

The image processor 520 generates a tomography image of the first target phase by using the determined motion correction value in reconstruction. The motion correction value may be, for example, a 2D or 3D motion vector. Motion correction reconstruction is performed by using a motion vector in back-projection in a reconstruction process. For example, the image processor 520 generates a tomography image set whose motion is corrected by using a 3D motion vector when a sinogram is reconstructed.

The image processor 520 reconstructs a second tomography image by applying the motion correction value to a process of reconstructing the second tomography image from the raw data. For example, the image processor 520 may reconstruct the second tomography image by using a motion vector corresponding to the first target phase as a motion correction value and by applying a motion vector corresponding to the first target phase in a reconstruction process. The motion correction value may be defined for non-continuous points on an edge of the object. The image processor 520 may determine the edge of the object in the second tomography image by applying the motion correction value to the non-continuous points on the edge of the object and by using an interpolation method.

According to an embodiment, the image processor 520 may use information about a structure of the object in order to determine the edge of the object in the second tomography image. For example, when the object is the heart, the information about the structure of the object may include information about a position, a shape, and a state in each phase of each of organs such as right atrium, right ventricle, left atrium, left ventricle, main artery, main vein, pulmonary artery, pulmonary vein, and valves. The image processor 520 may determine the edge of the object in the second tomography image by using the information about the structure of the object when using the motion correction value in a reconstruction process.

Figure 15:
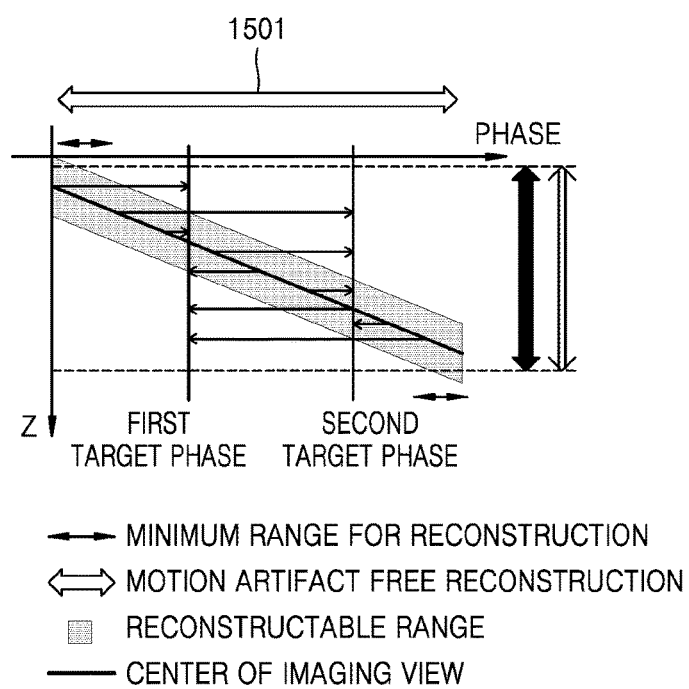
FIG. 15 illustrates a view for explaining a process of reconstructing a tomography image according to an embodiment.

FIG. 15 illustrates a view for explaining a process of reconstructing a tomography image according to an embodiment.

The tomography apparatus 100b according to embodiments may reconstruct a tomography image in an arbitrary phase for an arbitrary slice section by performing helical imaging for one cycle 1501 of motion of an object as shown in FIG. 15. For example, the tomography apparatus 100b may reconstruct a tomography image in a first target phase and a second target phase from raw data obtained by performing helical imaging for a period of time corresponding to the one cycle 1501 of motion of the object as shown in FIG. 15. Also, as shown in FIG. 15, since the tomography apparatus 100b may reconstruct a tomography image in an entire range in a z-axis direction for the first target phase and the second target range and reconstructable ranges of two phases are the same, more detailed medical information may be provided to a user.

Figure 16:
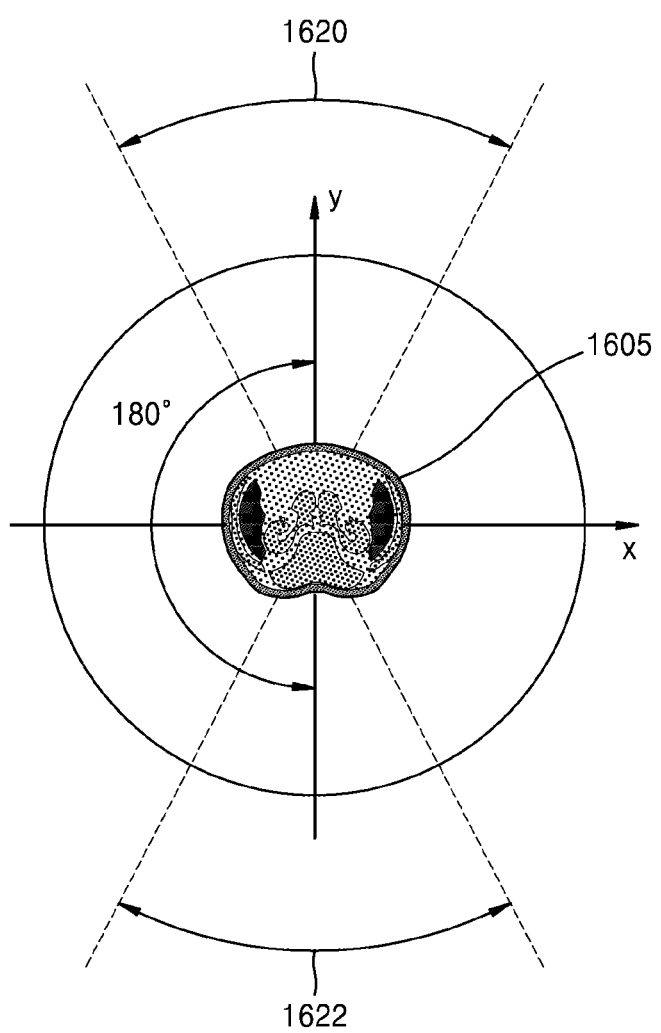
FIG. 16 illustrates a view for explaining a method of obtaining motion information according to an embodiment.

FIG. 16 illustrates a view for explaining a method of obtaining motion information according to an embodiment.

According to an embodiment, the image processor 520 obtains motion information by using a first image and a second image at conjugate angles that are angles facing each other. The first image and the second image are images having an angle difference 1610 of 180° on a rotation path. Also, the first image and the second image may be tomography images of slices corresponding to the same z-axis position within an error range of the object.

Referring to FIG. 16, a first angular section 1620 and a second angular section 1622 may have a relationship of conjugate angles that are angles facing each other. An angle difference between two angular sections that are in a conjugate angle relationship is 180°. Since the X-ray generator 106 rotates around an object at a predetermined speed, a first image and a second image reconstructed in the first angular section 1620 and the second angular section 1622 have a time difference due to the angle difference 1610 of 180°. The first image and the second image may be reconstructed from raw data by using a full reconstruction method, a half reconstruction method, or a partial reconstruction method according to angles of the first angular section 1620 and the second angular section 1622. Also, the first image and the second image may be complete images showing the whole of the object or incomplete images or partial images showing a part of the object according to angles of the first angular section 1620 and the second angular section 1622.

Once the first angular section 1620 and the second angular section 1622 have a conjugate angle relationship, since views in the first angular section 1620 and the second angular section 1622 are the same, a surface of an object 1605 detected when the object 1605 is imaged in the first angular section 1620 and a surface of the object 1605 detected when the object 1605 is imaged in the second angular section 1622 are the same. Accordingly, since the first image in the first angular section 1620 and the second image in the second angular section 1622 express states of the same surface of the object at different times, motion information of the object during a time difference due to the angle difference 1610 of 180° may be obtained by comparing the first image with the second image.

According to an embodiment, when the first angular section 1620 and the second angular section 1622 have values greater than 0° and less than 180°, the image processor 520 reconstructs the first image and the second image from raw data obtained in the first angular section 1620 and the second angular section 1622 by using a partial angle reconstruction (PAR) method. The image reconstructed by using the PAR method may be an incomplete image or a partial image. According to the present embodiment, since an image is reconstructed by using a relatively small angular section, unlike in a half reconstruction method or a full reconstruction method, a temporal resolution may be increased and motion artifacts may be minimized. Since the amount of motion of the object is measured by using the first image and the second image that are partial angle images in the present embodiment, the amount of motion of the object may be more accurately measured.

According to an embodiment, angular sections for obtaining the first image and the second image in order to obtain motion information may be determined according to a phase of a second tomography image to be reconstructed by using the motion information. When a second phase of the second tomography image is earlier than a first phase of a first tomography image, the first angular section 1620 may be set to correspond to the second phase. For example, the first angular section 1620 may be set so that a phase corresponding to the second phase is located at the center of the first angular section 1620. That is, since the second phase is earlier than the first phase, when motion information of the object for one cycle of motion is obtained from the second phase, a motion correction amount in the second phase may be obtained. Accordingly, the first angular section 1620 may be set to correspond to the second phase section. When the second phase of the second tomography image is later than the first phase of the first tomography image, the first angular section 1620 may be set to correspond to the first phase. For example, the first angular section 1620 may be set so that a phase corresponding to the first phase is located at the center of the first angular section 1620. That is, since the first phase is earlier than the second phase, when motion information of the object for one cycle of motion is obtained from the first phase, a motion correction amount in the second phase may be obtained. Accordingly, the first angular section 1620 may be set to correspond to the first phase section.

Figure 17:
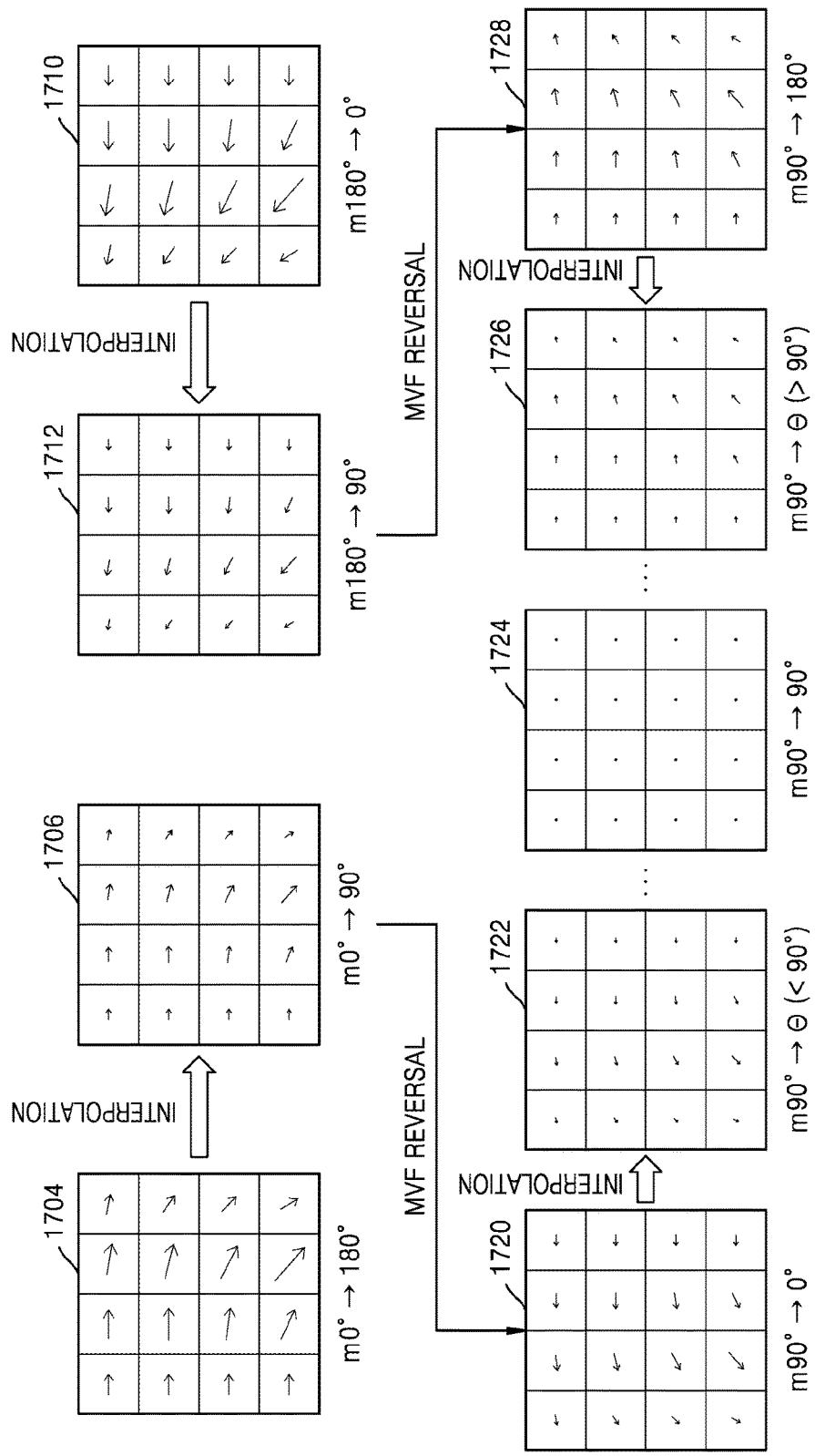
FIG. 17 illustrates motion information obtained by a method of obtaining motion information by imaging an object at conjugate angles, reconstructing images, and comparing the images according to an embodiment.

FIG. 17 illustrates motion information obtained by a method of obtaining motion information by imaging an object at conjugate angles, reconstructing images, and comparing the images according to an embodiment.

According to an embodiment, as described with reference to FIG. 16, a first image and a second image may be obtained in the first angular section 1620 and the second angular section 1622 that are in a conjugate angle relationship, and motion information that is expressed with a motion vector field (MVF) may be obtained by comparing the first image with the second image. The MVF includes motion vectors indicating a motion direction and a size based on positions of pixels of a tomography image.

In FIG. 17, an MVF is obtained from an image in a first angular section including 0° and a second angular section including 180°. The image processor 520 may obtain a first MVF 1704 and a second MVF 1710 in an angular section from 0° to 180° from the first image in the first angular section and the second image in the second angular section. A process of obtaining the first MVF 1704 and the second MVF 1710 may be performed by using a non-rigid registration method.

The image processor 520 may obtain a third MVF 1706 in an angular section from 0° to 90° by using an interpolation method from the first MVF 1704, and may obtain a fourth MVF 1712 in an angular section from 180° to 90° by using an interpolation method form the second MVF 1710. According to an embodiment, the image processor 520 may obtain an MVF in an angular section less than 180° by using an MVF in a section of 180° by using a linear interpolation method.

Furthermore, the image processor 520 reverses the third MVF 1706 to obtain a fifth MVF 1720 in an angular section from 90° to 0° and reverses the fourth MVF 1712 to obtain a sixth MVF 1728 in an angular section from 90° to 180°. Also, the image processor 520 may obtain a seventh MVF 1722 in an angular section from 90° to an intermediate angle less than 90° from the fifth MVF 1720 by using an interpolation method and may obtain an eighth MVF 1726 in an angular section from 90° to an intermediate angle greater than 90° and less than 180° from the sixth MVF 1728. In this manner, the image processor 520 may obtain an MVF between arbitrary two angular sections. Accordingly, the image processor 520 may determine two angle values of the X-ray detector 108 respectively corresponding to an imaging phase and a target phase, may obtain an MVF between the two angle values, and may obtain a motion correction value.

Figure 18:
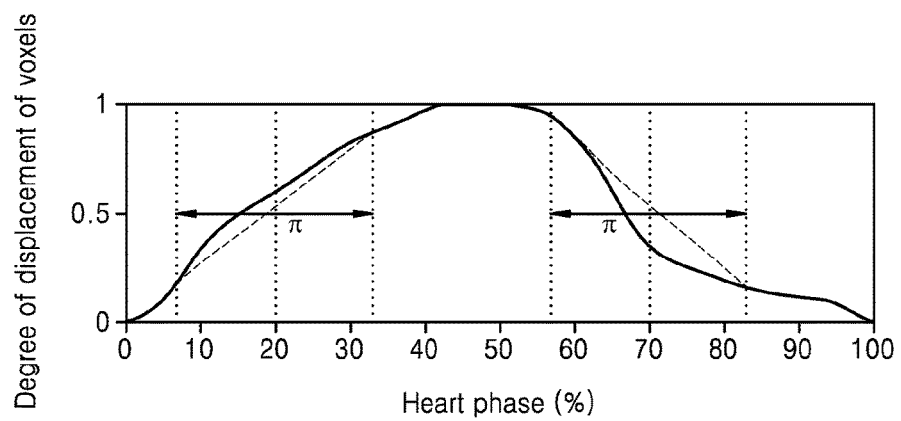
FIG. 18 illustrates a view for explaining a process of obtaining motion information from a motion model of an object according to an embodiment.

FIG. 18 illustrates a view for explaining a process of obtaining motion information from a motion model of an object according to an embodiment.

According to an embodiment, the image processor 520 may obtain motion information from a motion model of an object. The motion model of the object may be, for example, a respiration model or a heartbeat model. The motion model of the object may be expressed by using a function indicating a position of an edge of the object according to a time or an MVF according to a time.

FIG. 18 illustrates a heartbeat model. The heartbeat model shows a movement of a surface of the heart for one cycle of heartbeat including systole and diastole. In FIG. 18, a phase is expressed in a percentage (%) that is a ratio of a point to one cycle. As shown in FIG. 18, when one cycle of heartbeat and a rotation cycle of the X-ray detector 108 are matched to each other, a specific angle range may be displayed within one cycle.

The image processor 520 may obtain a size of a motion correction value in a predetermined phase section in the heartbeat model of FIG. 18 from an integral value in a phase section. Also, the image processor 520 may determine a direction of the motion correction value in the predetermined phase section from a direction of a motion vector component in a slice.

According to an embodiment, the image processor 520 may obtain motion information by using a user input. According to a method using a user input, for example, a user may designate corresponding points of an object in a tomography image set that is reconstructed in a plurality of phases and may obtain motion information by using phase information and information about the designated points. The points designated by the user may be points corresponding to an edge portion of the object, and the tomography apparatus 100*b* may provide a graphical user interface (GUI) including a guide in order for the user to designate the points corresponding to the edge portion.

Figure 19:
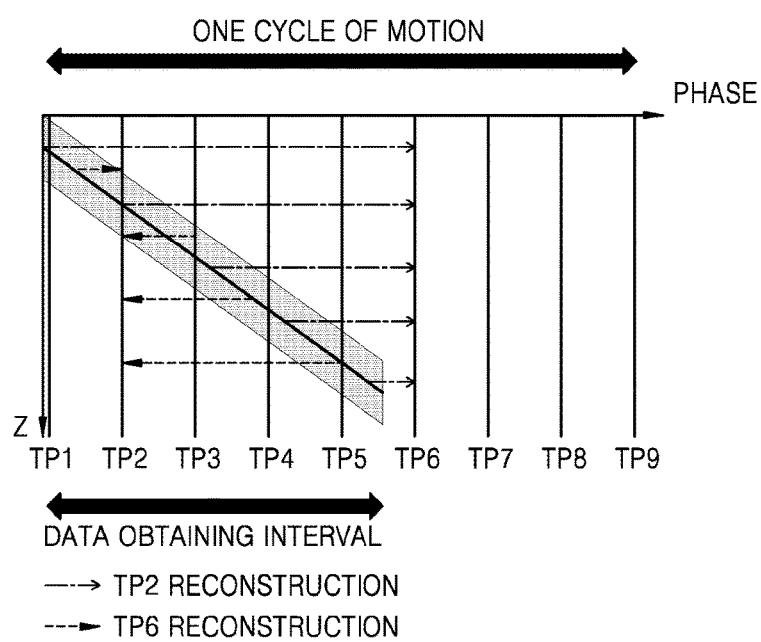
FIG. 19 illustrates a view for explaining a method of reconstructing an image according to an embodiment.

FIG. 19 illustrates a view for explaining a method of reconstructing an image according to an embodiment.

According to an embodiment, the tomography apparatus 100*b* may perform imaging in a first phase range that is shorter than one cycle of motion of an object and may reconstruct a tomography image in a phase beyond the first phase range from raw data obtained in the first phase range. For example, the image processor 520 may reconstruct a tomography image in a phase TP6 that is not included in the first phase range from obtained raw data as shown in FIG. 19. Accordingly, the image processor 520 may reconstruct a tomography image in phases (e.g., TP6, TP7, TP8, and TP9) beyond the first phase range as well as a tomography image in phases (e.g., TP1, TP2, TP3, TP4, and TP5) within the first phase range by reconstructing a tomography image of a target slice section in the first phase range and using motion information.

Figure 20:
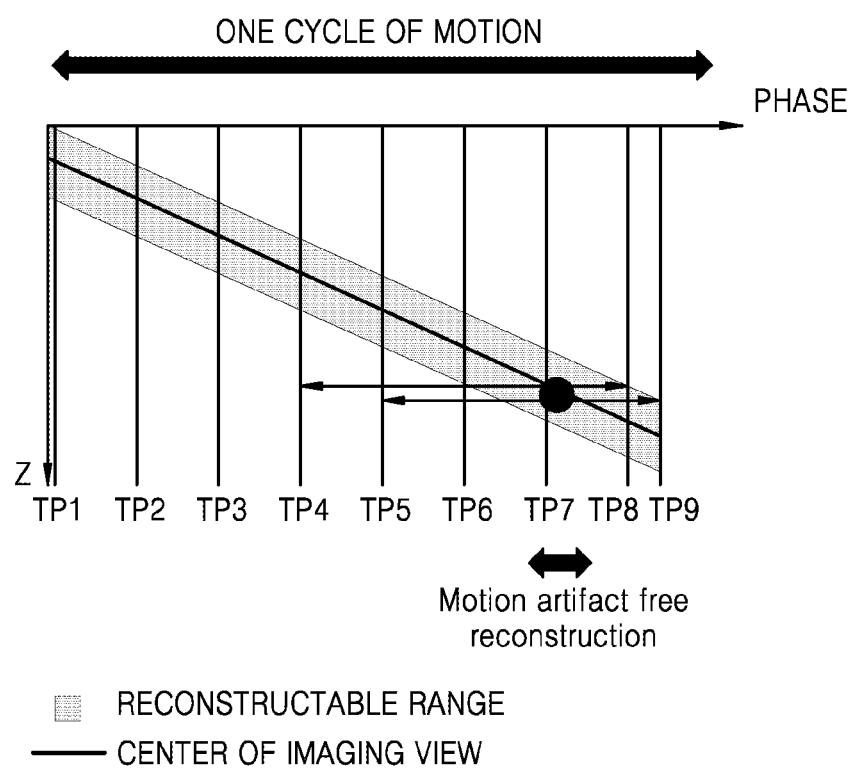
FIG. 20 illustrates a view for explaining a method of reconstructing an image according to an embodiment.

FIG. 20 illustrates a view for explaining a method of reconstructing an image according to an embodiment.

According to an embodiment, the image processor 520 may reconstruct tomography images in a plurality of target phases that are not included in a reconstructable phase section as well as a first tomography image in a phase included in the reconstructable phase section from raw data. According to embodiments, since a tomography image may be reconstructed in all phases, once raw data for a predetermined slice section in a phase section is obtained, a tomography image in an entire phase range may be reconstructed. Accordingly, once an entire region of an object is scanned at a high pitch, a tomography image in all phases may be reconstructed, thereby greatly reducing an imaging time and reducing patient inconvenience.

Figure 21:
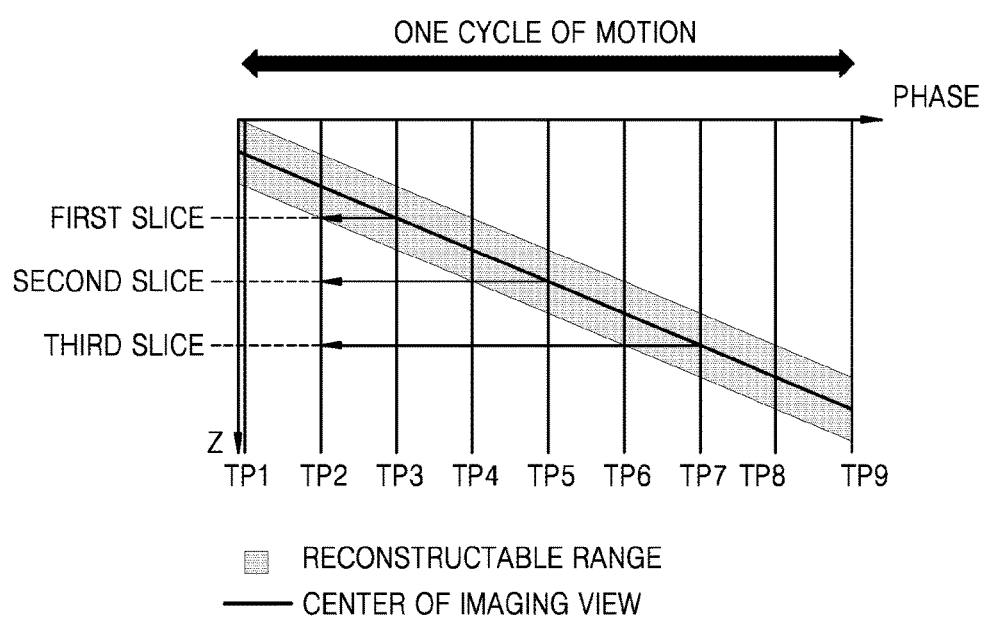
FIG. 21 illustrates a view for explaining a method of reconstructing an image according to an embodiment.

FIG. 21 illustrates a view for explaining a method of reconstructing an image according to an embodiment.

According to an embodiment, the image processor 520 may reconstruct a tomography image for a slice section over an entire region of an object in a predetermined phase by scanning the entire region of the object only one time. For example, as shown in FIG. 21, when a tomography image for a first slice section may be reconstructed from raw data in a target phase TP2 and a tomography image for a second slice section and a third slice section may not be reconstructed, the image processor 520 may reconstruct a fourth tomography image corresponding to the second slice section in the target phase TP2 and a fifth tomography image corresponding to the third slice section in the target phase TP2. In detail, the image processor 520 obtains a motion correction value corresponding to a phase difference between TP5 and TP2, and obtains the fourth tomography image in the target phase TP2 by using the motion correction value in a reconstruction process. Also, the image processor 520 obtains a motion correction value corresponding to a phase difference between TP7 and TP2, and obtains the fifth tomography image in the target phase TP2 by using the motion correction value in a reconstruction process. As such, the tomography apparatus 100*b* according to embodiments may obtain a tomography image for a slice section over an entire region of an imaged object from raw data.

Figure 22:
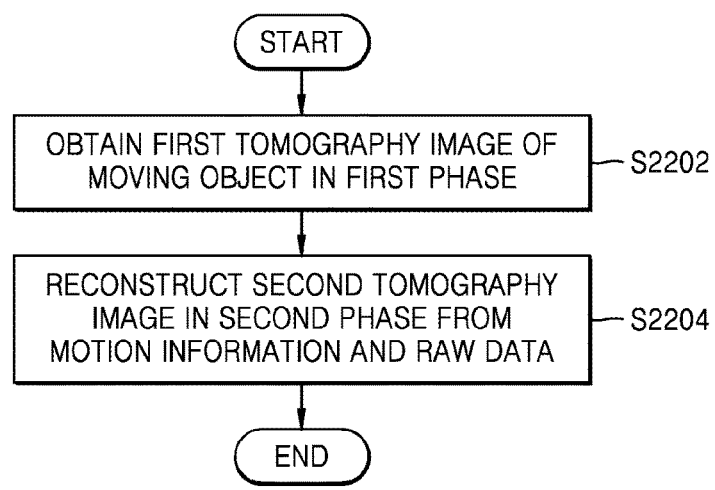
FIG. 22 illustrates a flowchart of a method of reconstructing a tomography image according to an embodiment.

FIG. 22 illustrates a flowchart of a method of reconstructing a tomography image according to an embodiment.

Operations of the method of reconstructing the tomography image may be performed by a tomography apparatus that may reconstruct a tomography image by imaging an object. The following will be explained on the assumption that a tomography apparatus 100 (which is any tomography apparatus in the specification) performs the method of reconstructing the tomography image. Accordingly, the description of the tomography apparatus 100 may apply to the method of reconstructing the tomography image, and the description of the method of reconstructing the tomography image may also apply to the tomography apparatus 100. Although the method of reconstructing the tomography image according to embodiments is performed by the tomography apparatus 100, the concept is not limited thereto and the method of reconstructing the tomography image may be performed by any of various tomography apparatuses.

In operation S2202, the data obtainer 510 obtains raw data of an object that moves by performing a tomography scan on the object. The data obtainer 510 may image the object by performing helical imaging. While the tomography scan is performed, the X-ray generator 106 helically rotates around the object and projection data or a sinogram may be obtained as raw data of the object.

Next, in operation S2204, the image processor 520 reconstructs a first tomography image of the object for a first slice section in a first phase from the raw data. For example, the image processor 520 may reconstruct the first tomography image by filtering the sinogram and then performing filtered back-projection.

Next, in operation S2206, a second tomography image of the object in a second phase for the first slice section is reconstructed by using the raw data and motion information. The second phase may be a phase beyond a phase range in which reconstruction may be performed from the raw data.

Figure 23:
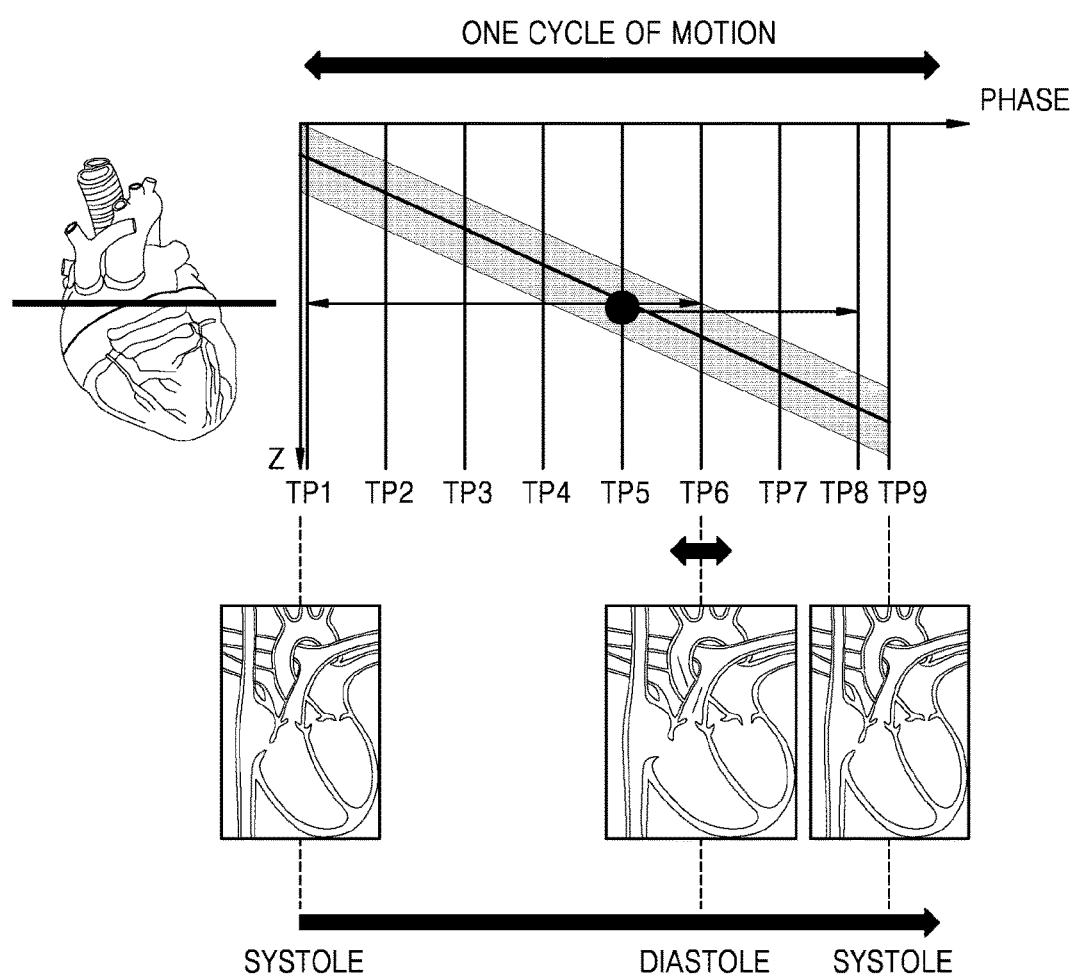
FIG. 23 illustrates a view for explaining a process of reconstructing a tomography image when an object is the heart according to an embodiment.

FIG. 23 illustrates a view for explaining a process of reconstructing a tomography image when an object is the heart according to an embodiment.

According to an embodiment, the object is the heart that periodically moves. The image processor 520 may reconstruct a tomography image of the heart for an arbitrary slice section in an arbitrary phase from raw data obtained by scanning an entire region of the heart by using 3D motion information related to a heartbeat.

According to an embodiment, the image processor may reconstruct a systolic image and a diastolic image of the heart and may determine a myocardial bridge by comparing the systolic image with the diastolic image. The systolic image and the diastolic image may be 3D images or a tomography image set. The myocardial bridge occurs when one of coronary arteries, which normally rest on top of the heart muscle, tunnels through the heart muscle rather than resting on top of the heart muscle, and thus when the heart squeezes, the muscle exerts pressure and constricts the artery, thereby leading to poor circulation of blood. The myocardial bridge may be diagnosed by comparing a systolic tomography image and a diastolic tomography image of the heart. For example, the myocardial bridge may be diagnosed by showing a 3D image along the coronary arteries and comparing the systolic tomography image and the diastolic tomography image. However, in order to obtain both the systolic tomography image and the diastolic tomography image of the heart, a pitch has to be sufficiently low, and thus an imaging time is increased. The tomography apparatus 100 according to the present embodiment may scan and image the heart at a high pitch and then may reconstruct a tomography image in systole and a tomography image in diastole by using 3D motion information of the heart.

Figure 24:
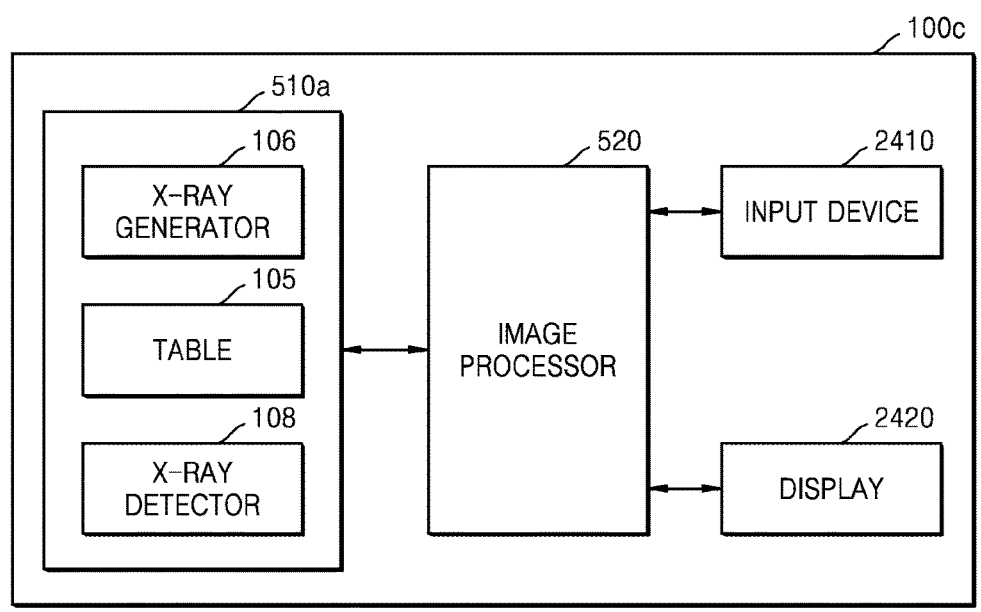
FIG. 24 illustrates a block diagram of a structure of a tomography apparatus according to an embodiment.

FIG. 24 illustrates a block diagram of a structure of a tomography apparatus 100c according to an embodiment.

The tomography apparatus 100c according to the present embodiment includes a data obtainer 510a, the image processor 520, an input device 2410, and a display 2420.

The data obtainer 510a according to the present embodiment includes the X-ray generator 106, the table 105, and the X-ray detector 108. As described with reference to FIG. 7, when the object 710 is placed on the table 105, the data obtainer 510a may perform a tomography scan on the object 710 as the X-ray generator 106 rotates along a circular trajectory in a gantry and the table 105 moves in a z-axis direction. The X-ray detector 108 generates raw data by detecting X-rays irradiated from the X-ray generator 106 and transmitted through the object 710.

The image processor 520 receives the raw data from the data obtainer 510a and reconstructs a first tomography image in a first phase for a first slice section of the object 710 from the raw data. Also, the image processor 520 reconstructs a second tomography image indicating a state of the object 710 in a second phase for the first slice section by using the raw data and 3D motion information of the object 710.

The input device 2410 receives a control signal from a user. For example, the input device 2410 may receive a control signal for controlling an operation of the tomography apparatus 100c or a control signal for changing information displayed on the display 2420 of the tomography apparatus 100c.

According to an embodiment, the input device 2410 may receive a control signal indicating a position of a slice section for generating a tomography image, a phase for generating a tomography image, or a combination thereof from the user. The image processor 520 receives the control signal of the user received from the input device 2410, reconstructs a second tomography image corresponding to a slice section or a phase selected by the user from the raw data, and displays the reconstructed tomography image on the display 2420.

When a position of a slice section is selected by the user, the image processor 520 may reconstruct a second tomography image corresponding to the selected slice section in a first phase corresponding to the first tomography image. For example, the image processor 520 reconstructs the second tomography image in the first phase for the selected slice section by using motion information and the raw data for the selected slice section from the raw data.

When a phase is selected by the user, the image processor 520 may reconstruct the second tomography image corresponding to the selected phase for a slice section corresponding to the first tomography image. For example, the image processor 520 reconstructs the second tomography image in the phase selected by the user by using the motion information and the raw data.

If both a position of a slice section and a phase are selected by the user, the image processor 520 reconstructs the second tomography image for the selected phase and the selected slice section by using the raw data and the motion information for the selected position of the slice section.

The display 2420 displays the reconstructed first tomography image and the reconstructed second tomography image. Also, the display 2420 may display an operation state of the tomography apparatus 100c, a GUI screen, and stored data.

The tomography apparatus 100c of FIG. 24 may correspond to the CT system 100a of FIG. 2. The input device 2410 of FIG. 24 may correspond to the input device 128 of FIG. 2. The display 2420 of FIG. 24 may correspond to the display 130 of FIG. 2.

Figure 25:
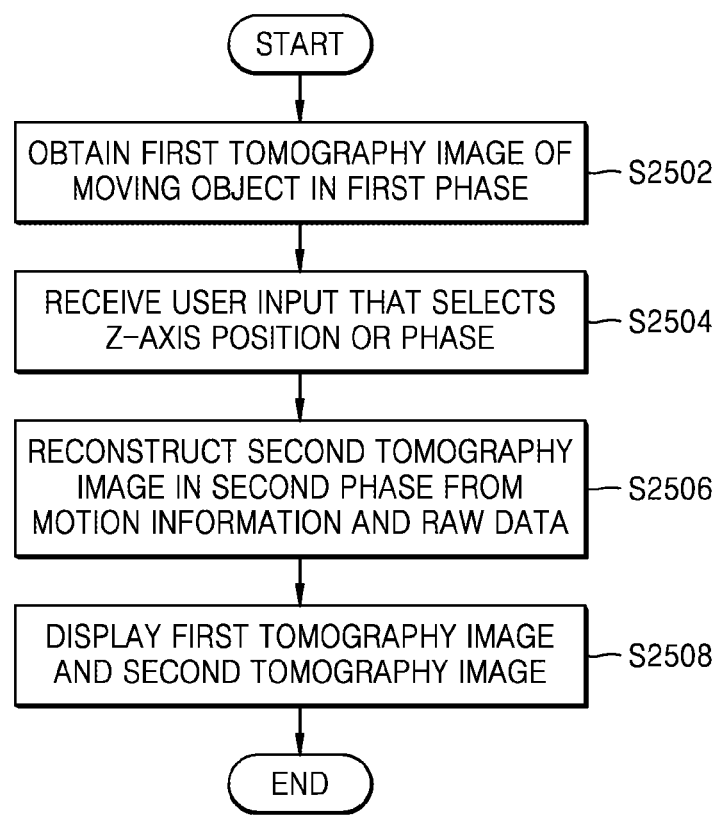
FIG. 25 illustrates a flowchart of a method of reconstructing a tomography image according to an embodiment.

FIG. 25 illustrates a flowchart of a method of reconstructing a tomography image according to an embodiment.

In operation S2502, the data obtainer 510a obtains raw data of an object that moves by performing a tomography scan on the object.

Next, in operation S2504, the image processor 520 reconstructs a first tomography image of the object for a first slice section in a first phase from the raw data.

In operation S2506, a user input that selects a position of a slice section or a phase is received from the input device 2410. In operation S2508, the image processor 520 reconstructs a second tomography image for the phase or the position of the slice section selected by the user. In operation S2510, the display 2420 displays the reconstructed first tomography image and the reconstructed second tomography image.

Figure 26:
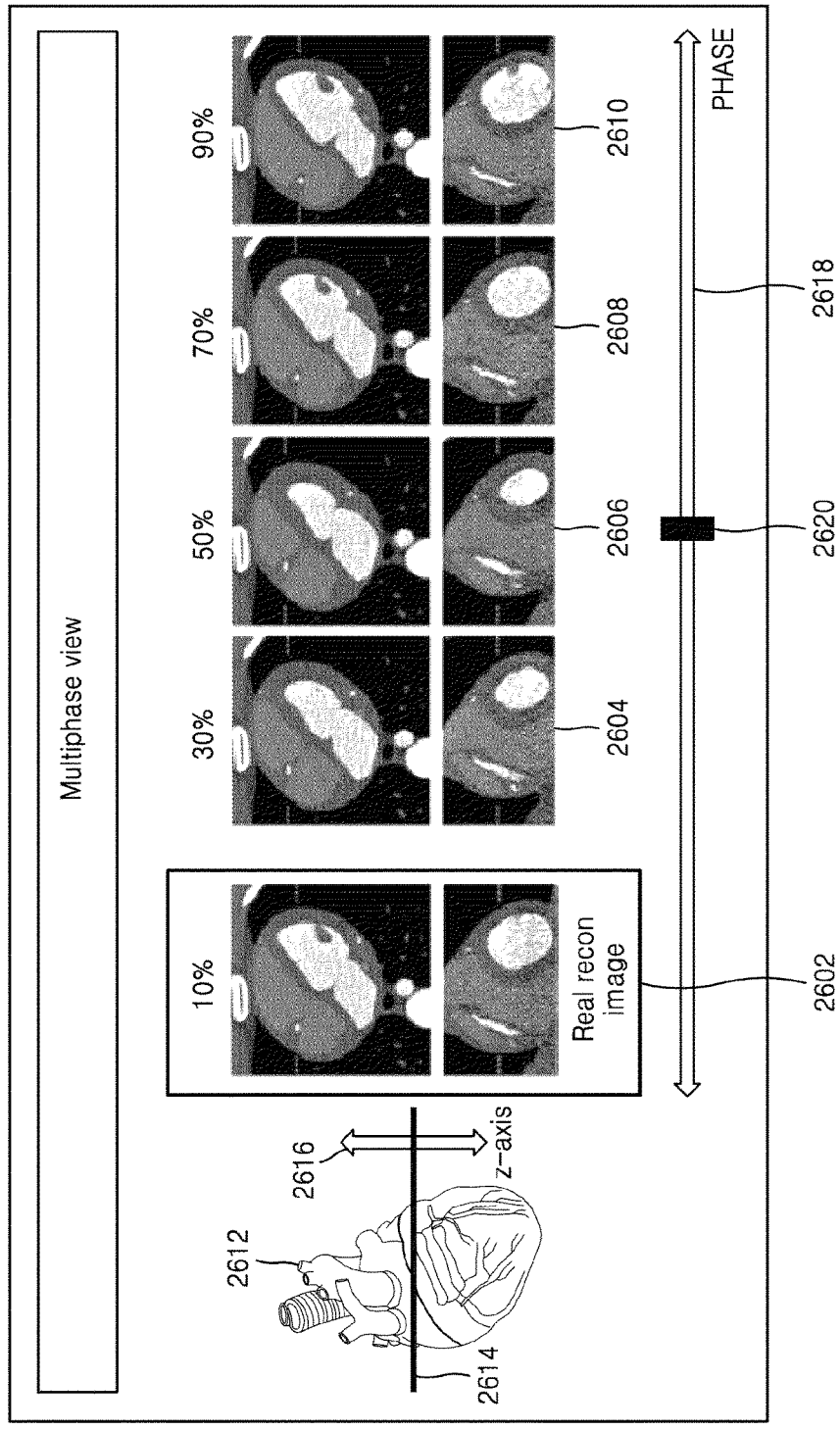
FIG. 26 illustrates a graphical user interface (GUI) view obtained when a user selects a phase or a position of a slice section according to an embodiment.

FIG. 26 illustrates a GUI view when a user selects a phase or a position of a slice section according to an embodiment.

According to an embodiment, as shown in FIG. 26, a GUI via which the user may select, within a predetermined range 2616, a position of a slice section 2614 for reconstructing a tomography image of an object 2612 that moves may be provided. Also, a GUI via which the user may select, within a predetermined phase range 2618, a phase for reconstructing a tomography image may be provided.

According to an embodiment, as shown in FIG. 26, a tomography image 2602 that is reconstructed from raw data may be displayed to be distinguished from tomography images 2604, 2606, 2608, and 2610 that are reconstructed by using motion information. As shown in FIG. 26, the plurality of tomography images 2604, 2606, 2608, and 2610 in different phases of 30%, 50%, 70%, and 90% reconstructed by applying motion information to the tomography image 2602 reconstructed from raw data may be displayed on a GUI.

Through the GUI according to the present embodiment, the user may freely select a phase and a position of a slice section for obtaining a tomography image, and the tomography apparatus 100c may perform reconstruction for the phase and the position of the slice section selected by the user in an entire phase range and all slice sections and may provide a result of the reconstruction.

According to the one or more embodiments, a tomography image in a target phase may be obtained by imaging an object that moves without restrictions of imaging times.

Also, according to the one or more embodiments, skewness and motion artifacts in a tomography image may be minimized by imaging an object that moves at a high pitch and reconstructing an image in a target phase through motion compensation.

Also, according to the one or more embodiments, an image in a wide z-axis range and various phases may be reconstructed even when an object that moves is imaged at a high pitch.

The afore-described embodiments may be implemented as an executable program, and may be executed by a general-purpose digital computer that runs the program by using a computer-readable recording medium. The computer-readable recording medium may be implemented by a transitory or non-transitory computer-readable recording medium.

Examples of the computer-readable recording medium include storage media such as magnetic storage media (e.g., read only memories (ROMs), floppy discs, or hard discs), optically readable media (e.g., compact disk-read only memories (CD-ROMs), or digital versatile disks (DVDs)), etc.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A tomography apparatus comprising:
a data obtainer configured to perform a tomography scan on a moving object and obtain raw data of the object; and
an image processor configured to:
reconstruct a first tomography image of the object for a first slice section in a first phase from the raw data; and
reconstruct a second tomography image in a second phase, which is different from the first phase, for the first slice section of the object by using the raw data and motion information indicating a three-dimensional (3D) motion of the object,
wherein the second phase is a phase beyond a phase range of the raw data.

2. The tomography apparatus of claim 1, wherein:
the data obtainer is configured to perform a tomography scan on the object over an angular range including at least one pair of facing angular sections, and
the image processor is configured to:
reconstruct one pair of images corresponding to the at least one pair of facing angular sections by using the raw data; and
obtain the motion information by using the one pair of images.

3. The tomography apparatus of claim 1, wherein:
the data obtainer is configured to obtain the raw data in a first phase range that is shorter than one cycle of motion of the object, and
the image processor is configured to reconstruct a plurality of the second tomography images having different phases from each other in the one cycle of motion of the object from the raw data.

4. The tomography apparatus of claim 1, wherein the object is a heart.

5. The tomography apparatus of claim 1, wherein the first phase is a phase with a lowest motion speed in one cycle of motion of the object.

6. The tomography apparatus of claim 1, wherein the motion information of the object is previously stored.

7. The tomography apparatus of claim 1, further comprising:
a display configured to display the first tomography image; and
an input device configured to receive a user input that selects a phase,
wherein the image processor is configured to reconstruct the second tomography image of the object in the second phase, which is different from the first phase, in response to the user input that selects the second phase, and
wherein the display is configured to display the second tomography image.

8. The tomography apparatus of claim 1, wherein the data obtainer comprises:
   a table configured to move the object along a first axis;
   an X-ray generator configured to:
      rotate around the object at a constant speed on a plane perpendicular to the first axis; and
      irradiate X-rays; and
   an X-ray detector configured to detect the X-rays,
   wherein the data obtainer is configured to obtain the raw data by detecting the irradiated X-rays in the X-ray detector while the object is moved along the first axis and the X-ray generator rotates around the object.

9. The tomography apparatus of claim 8, further comprising:
   a display configured to display the first tomography image; and
   an input device configured to receive a user input that selects at least one of a phase and a position of the object on the first axis,
   wherein the image processor is configured to reconstruct a tomography image in the selected phase from a tomography image in the first phase obtained at the selected position on the first axis, and
   wherein the display is configured to display the second tomography image.

10. The tomography apparatus of claim 1, wherein the object is a heart, and
   wherein the image processor is configured to:
      reconstruct a diastolic tomography image corresponding to diastole of the heart as the first tomography image in the first phase;
      reconstruct a systolic tomography image corresponding to systole of the heart as the second tomography image in the second phase; and
      determine whether a myocardial bridge occurs by comparing the diastolic tomography image with the systolic tomography image.

11. A method of reconstructing a tomography image, the method comprising:
   performing a tomography scan on a moving object and obtaining raw data of the object;
   reconstructing a first tomography image of the object for a first slice section in a first phase from the raw data; and
   reconstructing a second tomography image in a second phase, which is different from the first phase, for the first slice section of the object by using the raw data and motion information indicating a three-dimensional (3D) motion of the object,
   wherein the second phase is a phase beyond a phase range of the raw data.

12. The method of claim 11, further comprising:
   performing a tomography scan on the object and obtaining over an angular range including at least one pair of facing angular sections;
   reconstructing one pair of images corresponding to the at least one pair of facing angular sections by using the raw data; and
   obtaining the motion information by using the one pair of images.

13. The method of claim 11, further comprising:
   obtaining the raw data in a first phase range that is shorter than one cycle of motion of the object; and
   reconstructing a plurality of the second tomography images having different phases from each other in the one cycle of the motion of the object from the raw data.

14. The method of claim 11, wherein the object is a heart.

15. The method of claim 11, wherein the first phase is a phase with a lowest motion speed in one cycle of motion of the object.

16. The method of claim 11, wherein the motion information of the object is previously stored.

17. The method of claim 11, further comprising:
   receiving a user input that selects a phase;
   reconstructing the second tomography image of the object in the second phase, which is different from the first phase, in response to the user input that selects the second phase; and
   displaying the second tomography image.

18. The method of claim 11, wherein the performing the tomography scan comprises obtaining the raw data by detecting irradiated X-rays while the object is moved along a first axis and a X-ray generator rotates around the object.

19. The method of claim 18, further comprising:
   receiving a user input that selects at least one of a phase and a position of the object on the first axis;
   reconstructing a tomography image in the selected phase from a tomography image in the first phase obtained at the selected position on the first axis; and
   displaying the second tomography image.

20. A computer-readable recording medium storing a program code when executed performs a method of reconstructing a tomography image, the method comprising:
   performing a tomography scan on a moving object and obtaining raw data of the object;
   reconstructing a first tomography image of the object for a first slice section in a first phase from the raw data; and
   reconstructing a second tomography image in a second phase, which is different from the first phase, for the first slice section of the object by using the raw data and motion information indicating a three-dimensional (3D) motion of the object,
   wherein the second phase is a phase beyond a phase range of the raw data.

* * * * *